United States Patent
Shah et al.

(10) Patent No.: US 11,883,626 B2
(45) Date of Patent: Jan. 30, 2024

(54) DETECTION OF AN ENDOSCOPE TO A FLUID MANAGEMENT SYSTEM

(71) Applicant: BOSTON SCIENTIFIC SCIMED, INC., Maple Grove, MN (US)

(72) Inventors: Vivek Shah, Reading, MA (US); Peter J. Pereira, Mendon, MA (US); Niraj Prasad Rauniyar, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 286 days.

(21) Appl. No.: 16/911,611

(22) Filed: Jun. 25, 2020

(65) Prior Publication Data
US 2020/0405955 A1    Dec. 31, 2020

Related U.S. Application Data

(60) Provisional application No. 62/867,557, filed on Jun. 27, 2019.

(51) Int. Cl.
| A61M 5/142 | (2006.01) |
| A61M 5/168 | (2006.01) |
| A61M 5/172 | (2006.01) |

(52) U.S. Cl.
CPC ........ *A61M 5/142* (2013.01); *A61M 5/14228* (2013.01); *A61M 5/16859* (2013.01);
(Continued)

(58) Field of Classification Search
CPC .......... A61M 5/16859; A61M 5/14228; A61M 2005/1726; A61M 2205/0227;
(Continued)

(56) References Cited

U.S. PATENT DOCUMENTS

| 3,064,649 A | 11/1962 | Lee |
| 3,770,129 A | 11/1973 | Brumfield et al. |

(Continued)

FOREIGN PATENT DOCUMENTS

| EP | 0153190 A1 | 8/1985 |
| EP | 0331505 A1 | 9/1989 |

(Continued)

OTHER PUBLICATIONS

"AAGL Practice Report: Practice Guidelines for the Management of Hysteroscopic Distending Media," (Replaces Hysteroscopic Fluid Monitoring Guidelines. J Am Assoc Gynecol Laparosc. 2000; 167-168) J Minim Invasive Gynecol. vol. 20:137-48, Mar.-Apr. 2013; doi: 10,1016/j.jmig.2012.12.002.

(Continued)

*Primary Examiner* — Shefali D Patel
(74) *Attorney, Agent, or Firm* — Seager, Tufte & Wickhem, LLP

(57) ABSTRACT

A fluid management and medical device system may include a fluid management system and a medical device. The fluid management system may include a pump configured to pump fluid to the medical device and a processing device configured to control the pump to maintain a target fluid flow range. The medical device may include an elongate shaft in fluid communication with the pump of the fluid management system, a pressure sensor, and a workstation in electronic communication with the pressure sensor and the processing device of the fluid management system. The processing device may be configured to adjust a fluid flow rate based on data received from the pressure sensor of the medical device and configured to verify the medical device is in a patient's body prior to adjusting the fluid flow rate based on the data received from the pressure sensor.

18 Claims, 18 Drawing Sheets

(52) U.S. Cl.
CPC ...... *A61M 5/16877* (2013.01); *A61M 5/1723* (2013.01); *A61M 2205/3334* (2013.01); *A61M 2205/3368* (2013.01); *A61M 2205/502* (2013.01)

(58) Field of Classification Search
CPC .. A61M 2205/3331; A61M 2205/3334; A61M 2205/3344; A61M 2205/3368; A61M 2205/3379; A61M 2205/50; A61M 2205/502; A61M 2230/30; A61M 5/142; A61M 5/16854; A61M 5/1723; A61M 5/48; A61M 5/486; A61M 5/16877; A61M 2205/60; A61B 1/0008; A61B 1/00097; A61B 1/015; A61B 2218/001; A61B 2218/002; A61B 2562/06; A61B 5/01; A61B 5/02; A61B 5/021; A61B 5/02108; A61B 5/02116; A61B 5/02141; A61B 5/0215; A61B 5/02158; A61B 5/03; A61B 5/036; A61B 5/68; A61B 5/6846; A61B 5/6847; A61B 5/6885

See application file for complete search history.

(56) References Cited

U.S. PATENT DOCUMENTS

| | | | |
|---|---|---|---|
| 3,835,842 A | 9/1974 | Iglesias | |
| 3,850,162 A | 11/1974 | Iglesias | |
| 3,877,433 A | 4/1975 | Librach | |
| 3,900,022 A | 8/1975 | Widran | |
| 3,945,375 A | 3/1976 | Banko | |
| 4,092,246 A | 5/1978 | Kummer | |
| 4,180,074 A | 12/1979 | Murry et al. | |
| 4,203,444 A | 5/1980 | Bonnell et al. | |
| 4,261,360 A | 4/1981 | Perez | |
| 4,278,078 A | 7/1981 | Smith | |
| 4,369,768 A | 1/1983 | Vukovic | |
| 4,384,580 A | 5/1983 | Leviton | |
| 4,388,922 A | 6/1983 | Telang | |
| 4,395,258 A | 7/1983 | Wang et al. | |
| 4,400,168 A | 8/1983 | Buechel et al. | |
| 4,449,538 A | 5/1984 | Corbitt et al. | |
| 4,475,901 A | 10/1984 | Kraegen et al. | |
| 4,606,330 A | 8/1986 | Bonnett | |
| 4,650,461 A | 3/1987 | Woods | |
| 4,650,462 A | 3/1987 | DeSatnick et al. | |
| 4,650,464 A | 3/1987 | Ruiz et al. | |
| 4,655,197 A | 4/1987 | Atkinson | |
| 4,671,792 A | 6/1987 | Borsanyi | |
| 4,678,459 A | 7/1987 | Onik et al. | |
| 4,700,694 A | 10/1987 | Shishido | |
| 4,712,567 A | 12/1987 | Gille et al. | |
| 4,735,603 A | 4/1988 | Goodson et al. | |
| 4,838,856 A | 6/1989 | Mulreany | |
| 4,844,074 A | 7/1989 | Kurucz | |
| 4,902,276 A | 2/1990 | Zakko | |
| 4,902,277 A | 2/1990 | Mathies et al. | |
| 4,921,477 A | 5/1990 | Davis | |
| 4,930,997 A | 6/1990 | Bennett | |
| 4,933,843 A | 6/1990 | Scheller et al. | |
| RE33,258 E | 7/1990 | Onik et al. | |
| 4,955,882 A | 9/1990 | Hakky | |
| 4,971,034 A | 11/1990 | Doi et al. | |
| 4,994,026 A | 2/1991 | Fecondini | |
| 4,998,527 A | 3/1991 | Meyer | |
| 4,998,914 A | 3/1991 | Wiest et al. | |
| 5,009,656 A | 4/1991 | Reimels | |
| 5,041,096 A | 8/1991 | Beuchat et al. | |
| 5,053,002 A | 10/1991 | Barlow | |
| 5,080,660 A | 1/1992 | Buelna | |
| 5,085,658 A | 2/1992 | Meyer | |
| 5,098,375 A | 3/1992 | Baier | |
| 5,106,364 A | 4/1992 | Hayafuji et al. | |
| 5,152,745 A | 10/1992 | Steiner et al. | |
| 5,152,746 A | 10/1992 | Atkinson et al. | |
| 5,169,397 A | 12/1992 | Sakashita et al. | |
| 5,178,606 A | 1/1993 | Ognier et al. | |
| 5,180,896 A | 1/1993 | Gibby et al. | |
| 5,195,541 A | 3/1993 | Obenchain | |
| 5,213,571 A | 5/1993 | Fujio et al. | |
| 5,217,466 A | 6/1993 | Hasson | |
| 5,217,479 A | 6/1993 | Shuler | |
| 5,277,696 A | 1/1994 | Hagen | |
| 5,312,399 A | 5/1994 | Hakky et al. | |
| 5,320,091 A | 6/1994 | Grossi et al. | |
| 5,322,506 A * | 6/1994 | Kullas | A61M 3/0216 604/27 |
| 5,360,396 A | 11/1994 | Chan | |
| 5,381,510 A | 1/1995 | Ford et al. | |
| 5,382,229 A | 1/1995 | Grabenkort et al. | |
| 5,403,276 A | 4/1995 | Schechter et al. | |
| 5,403,277 A | 4/1995 | Dodge et al. | |
| 5,403,311 A | 4/1995 | Abele et al. | |
| 5,437,629 A | 8/1995 | Goldrath | |
| 5,439,441 A | 8/1995 | Grimsley et al. | |
| 5,445,610 A | 8/1995 | Evert | |
| 5,456,689 A | 10/1995 | Kresch et al. | |
| 5,456,835 A | 10/1995 | Castino et al. | |
| 5,460,490 A | 10/1995 | Carr et al. | |
| 5,464,391 A | 11/1995 | Devale | |
| 5,470,324 A | 11/1995 | Cook et al. | |
| 5,476,368 A | 12/1995 | Rabenau et al. | |
| 5,476,447 A | 12/1995 | Noda et al. | |
| 5,483,951 A | 1/1996 | Frassica et al. | |
| 5,492,537 A | 2/1996 | Vancaillie | |
| 5,503,626 A | 4/1996 | Goldrath | |
| 5,514,091 A | 5/1996 | Yoon | |
| 5,520,638 A | 5/1996 | O'Quinn et al. | |
| 5,522,805 A | 6/1996 | Vancaille et al. | |
| 5,527,331 A | 6/1996 | Kresch et al. | |
| 5,536,234 A | 7/1996 | Newman | |
| 5,556,378 A | 9/1996 | Storz et al. | |
| 5,563,481 A | 10/1996 | Krause | |
| 5,569,188 A | 10/1996 | Mackool | |
| 5,571,389 A | 11/1996 | Kerampran | |
| 5,578,012 A | 11/1996 | Kamen et al. | |
| 5,586,973 A | 12/1996 | Lemaire et al. | |
| 5,599,301 A | 2/1997 | Jacobs et al. | |
| 5,602,449 A | 2/1997 | Krause et al. | |
| 5,605,545 A | 2/1997 | Nowosielski et al. | |
| 5,626,563 A | 5/1997 | Dodge et al. | |
| 5,630,798 A | 5/1997 | Beiser et al. | |
| 5,630,799 A | 5/1997 | Beiser et al. | |
| 5,643,203 A | 7/1997 | Beiser et al. | |
| 5,643,302 A | 7/1997 | Beiser et al. | |
| 5,656,027 A | 8/1997 | Ellingboe | |
| 5,662,611 A | 9/1997 | Beiser et al. | |
| 5,669,921 A | 9/1997 | Berman et al. | |
| 5,697,281 A | 12/1997 | Eggers et al. | |
| 5,709,670 A | 1/1998 | Vancaillie | |
| 5,730,752 A | 3/1998 | Alden et al. | |
| 5,733,263 A | 3/1998 | Wheatman | |
| 5,749,889 A | 5/1998 | Bacich et al. | |
| 5,759,185 A | 6/1998 | Grinberg | |
| 5,776,104 A | 7/1998 | Guignard et al. | |
| 5,800,381 A | 9/1998 | Ognier | |
| 5,800,383 A | 9/1998 | Chandler et al. | |
| 5,807,313 A | 9/1998 | Delk et al. | |
| 5,810,770 A | 9/1998 | Chin et al. | |
| 5,810,809 A | 9/1998 | Rydell | |
| 5,810,858 A | 9/1998 | Berman et al. | |
| 5,810,876 A | 9/1998 | Kelleher | |
| 5,814,009 A | 9/1998 | Wheatman | |
| 5,823,971 A | 10/1998 | Robinson et al. | |
| 5,823,990 A | 10/1998 | Henley | |
| 5,830,176 A | 11/1998 | Mackool | |
| 5,830,180 A | 11/1998 | Chandler et al. | |
| 5,836,909 A | 11/1998 | Cosmescu | |
| 5,840,060 A | 11/1998 | Beiser et al. | |
| 5,843,951 A | 12/1998 | Inoue | |
| 5,853,392 A | 12/1998 | Dennis | |
| 5,873,886 A | 2/1999 | Larsen et al. | |
| 5,875,282 A | 2/1999 | Jordan et al. | |

(56) References Cited

U.S. PATENT DOCUMENTS

| | | | |
|---|---|---|---|
| 5,882,339 A | 3/1999 | Beiser et al. |
| 5,885,277 A | 3/1999 | Korth |
| 5,902,264 A | 5/1999 | Toso et al. |
| 5,906,615 A | 5/1999 | Thompson |
| 5,919,218 A | 7/1999 | Carr |
| 5,921,953 A | 7/1999 | Novak et al. |
| 5,925,050 A | 7/1999 | Howard |
| 5,941,876 A | 8/1999 | Nardella et al. |
| 5,944,668 A | 8/1999 | Vancaillie et al. |
| 5,947,983 A | 9/1999 | Solar et al. |
| 5,956,130 A | 9/1999 | Vancaillie et al. |
| 5,960,160 A | 9/1999 | Clark et al. |
| 5,997,534 A | 12/1999 | Tu et al. |
| 6,004,319 A | 12/1999 | Goble et al. |
| 6,010,454 A | 1/2000 | Arieff et al. |
| 6,024,720 A | 2/2000 | Chandler et al. |
| 6,024,751 A | 2/2000 | Lovato et al. |
| 6,030,359 A | 2/2000 | Nowosielski |
| 6,032,673 A | 3/2000 | Savage et al. |
| 6,036,681 A | 3/2000 | Hooven |
| 6,039,748 A | 3/2000 | Savage et al. |
| 6,046,442 A | 4/2000 | Kawamura et al. |
| 6,052,060 A | 4/2000 | Butler et al. |
| 6,056,746 A | 5/2000 | Goble et al. |
| 6,077,246 A | 6/2000 | Kullas et al. |
| 6,090,106 A | 7/2000 | Goble et al. |
| 6,106,494 A | 8/2000 | Saravia et al. |
| 6,109,268 A | 8/2000 | Thapliyal et al. |
| 6,113,594 A | 9/2000 | Savage |
| RE36,914 E | 10/2000 | Carlsen et al. |
| 6,142,974 A | 11/2000 | Kistner et al. |
| 6,146,359 A | 11/2000 | Carr et al. |
| 6,149,620 A | 11/2000 | Baker et al. |
| 6,149,621 A | 11/2000 | Makihara |
| 6,159,160 A | 12/2000 | Hsei et al. |
| 6,176,847 B1 | 1/2001 | Humphreys et al. |
| 6,183,437 B1 | 2/2001 | Walker |
| 6,186,752 B1 | 2/2001 | Deniega et al. |
| 6,193,715 B1 | 2/2001 | Wrublewski et al. |
| 6,203,493 B1 * | 3/2001 | Ben-Haim ............ A61B 8/0833 600/117 |
| 6,206,014 B1 | 3/2001 | Cameron et al. |
| 6,213,970 B1 | 4/2001 | Nelson et al. |
| 6,238,366 B1 | 5/2001 | Savage et al. |
| 6,245,084 B1 | 6/2001 | Mark et al. |
| 6,257,265 B1 | 7/2001 | Brunner et al. |
| 6,259,074 B1 | 7/2001 | Brunner et al. |
| 6,261,261 B1 | 7/2001 | Gordon |
| 6,261,283 B1 | 7/2001 | Morgan et al. |
| 6,273,862 B1 | 8/2001 | Privitera et al. |
| 6,283,937 B1 | 9/2001 | Takamatsu et al. |
| 6,293,926 B1 | 9/2001 | Sorensen et al. |
| 6,293,942 B1 | 9/2001 | Goble et al. |
| 6,302,864 B1 | 10/2001 | Nowosielski |
| 6,319,221 B1 | 11/2001 | Savage et al. |
| 6,358,224 B1 | 3/2002 | Tims et al. |
| 6,358,263 B2 | 3/2002 | Mark et al. |
| 6,396,583 B1 | 5/2002 | Clare |
| 6,428,316 B1 | 8/2002 | Rodriquez |
| 6,432,113 B1 | 8/2002 | Parkin et al. |
| 6,478,805 B1 | 11/2002 | Marino et al. |
| 6,494,881 B1 | 12/2002 | Bales et al. |
| 6,512,212 B1 | 1/2003 | Leverne Harris |
| 6,527,743 B1 | 3/2003 | Fowler et al. |
| 6,527,745 B1 | 3/2003 | Kanda et al. |
| 6,554,780 B1 | 4/2003 | Sampson et al. |
| 6,554,791 B1 | 4/2003 | Cartledge et al. |
| 6,569,147 B1 | 5/2003 | Evans et al. |
| 6,572,641 B2 | 6/2003 | Brugger et al. |
| 6,585,708 B1 | 7/2003 | Maaskamp |
| 6,595,957 B1 | 7/2003 | Griffiths et al. |
| 6,599,277 B2 | 7/2003 | Neubert |
| 6,602,221 B1 | 8/2003 | Saravia et al. |
| 6,626,827 B1 | 9/2003 | Felix et al. |
| 6,629,986 B1 | 10/2003 | Ross et al. |
| 6,632,214 B2 | 10/2003 | Morgan et al. |
| 6,635,031 B2 | 10/2003 | Fowler et al. |
| 6,635,034 B1 | 10/2003 | Cosmescu |
| 6,685,667 B1 | 2/2004 | Delk et al. |
| 6,699,184 B2 | 3/2004 | Felix et al. |
| 6,712,759 B2 | 3/2004 | Muller |
| 6,740,074 B2 | 5/2004 | Morgan et al. |
| 6,743,184 B2 | 6/2004 | Sampson et al. |
| 6,746,439 B2 | 6/2004 | Lenker |
| 6,775,473 B2 | 8/2004 | Augustine et al. |
| 6,780,166 B2 | 8/2004 | Kanda et al. |
| 6,824,528 B1 | 11/2004 | Faries et al. |
| 6,832,996 B2 | 12/2004 | Woloszko et al. |
| 6,843,099 B2 | 1/2005 | Derek et al. |
| 6,872,183 B2 | 3/2005 | Sampson et al. |
| 6,875,194 B2 | 4/2005 | MacKool |
| 6,896,664 B2 | 5/2005 | Novak |
| 6,899,697 B2 | 5/2005 | Fowler et al. |
| 6,901,216 B2 | 5/2005 | Jusiak et al. |
| 6,908,451 B2 | 6/2005 | Brody et al. |
| 6,958,058 B1 | 10/2005 | Hunter, Sr. et al. |
| 6,972,009 B1 | 12/2005 | Stromberg et al. |
| 6,979,332 B2 | 12/2005 | Adams |
| 6,997,896 B2 | 2/2006 | Novak |
| 7,029,451 B2 | 4/2006 | Anderson et al. |
| 7,031,602 B2 | 4/2006 | Faries, Jr. et al. |
| 7,063,670 B2 | 6/2006 | Sampson et al. |
| 7,070,604 B1 | 7/2006 | Garito et al. |
| 7,083,601 B1 | 8/2006 | Cosmescu |
| 7,150,713 B2 | 12/2006 | Shener et al. |
| 7,153,285 B2 | 12/2006 | Lauman et al. |
| 7,164,852 B2 | 1/2007 | Cazzini et al. |
| 7,204,821 B1 | 4/2007 | Clare et al. |
| 7,207,966 B2 | 4/2007 | Savare et al. |
| 7,226,459 B2 | 6/2007 | Cesarini et al. |
| 7,232,457 B2 | 6/2007 | Schmidt et al. |
| 7,244,256 B2 | 7/2007 | DeCesare et al. |
| 7,249,602 B1 | 7/2007 | Emanuel |
| 7,273,359 B2 | 9/2007 | Blight et al. |
| 7,297,133 B2 | 11/2007 | Nelson et al. |
| 7,334,718 B2 | 2/2008 | McAlister et al. |
| 7,384,417 B2 | 6/2008 | Cucin |
| 7,394,976 B2 | 7/2008 | Entenman et al. |
| 7,458,951 B2 | 12/2008 | Lauman et al. |
| 7,481,936 B2 | 1/2009 | Gorsuch et al. |
| 7,510,535 B2 | 3/2009 | Hibner et al. |
| 7,549,987 B2 | 6/2009 | Shadduck |
| 7,591,794 B2 | 9/2009 | Lacoste et al. |
| 7,597,662 B2 | 10/2009 | Litscher et al. |
| 7,604,610 B2 | 10/2009 | Shener et al. |
| 7,621,898 B2 | 11/2009 | Lalomia et al. |
| 7,632,248 B2 | 12/2009 | Delk et al. |
| 7,674,259 B2 | 3/2010 | Shadduck |
| 7,678,070 B2 | 3/2010 | Kumar et al. |
| 7,695,447 B2 | 4/2010 | Khashayar et al. |
| 7,731,689 B2 | 6/2010 | Prisco et al. |
| 7,753,880 B2 | 7/2010 | Malackowski |
| 7,811,282 B2 | 10/2010 | McClurken |
| 7,815,634 B2 | 10/2010 | McClurken et al. |
| 7,865,072 B2 | 1/2011 | Cassidy |
| 7,867,188 B2 | 1/2011 | Frey |
| 7,867,191 B2 | 1/2011 | Suzuki |
| 7,892,229 B2 | 2/2011 | Shadduck et al. |
| 7,896,834 B2 | 3/2011 | Smisson, III et al. |
| 7,901,403 B2 | 3/2011 | Woloszko et al. |
| 7,918,822 B2 | 4/2011 | Kumar et al. |
| 7,930,575 B2 | 4/2011 | Suginaka et al. |
| 7,975,491 B2 | 7/2011 | Smisson, III et al. |
| 7,981,073 B2 | 7/2011 | Möllstam et al. |
| 8,052,644 B2 | 11/2011 | Radgowski et al. |
| 8,061,359 B2 | 11/2011 | Emanuel |
| 8,109,906 B2 | 2/2012 | Smisson, III et al. |
| 8,123,750 B2 | 2/2012 | Norton et al. |
| 8,142,718 B2 | 3/2012 | Tak et al. |
| 8,178,040 B2 | 5/2012 | Brauer |
| 8,206,342 B2 | 6/2012 | Hacker et al. |
| 8,206,345 B2 | 6/2012 | Abboud et al. |
| 8,219,982 B2 | 7/2012 | Harkanyi et al. |
| 8,225,643 B2 | 7/2012 | Abboud et al. |

(56) References Cited

U.S. PATENT DOCUMENTS

| | | |
|---|---|---|
| 8,226,549 B2 | 7/2012 | Kumar et al. |
| 8,262,603 B2 | 9/2012 | Shener et al. |
| 8,267,934 B2 | 9/2012 | Earley et al. |
| 8,287,485 B2 | 10/2012 | Kimura et al. |
| 8,308,726 B2 | 11/2012 | Kumar et al. |
| 8,313,460 B2 | 11/2012 | Cassidy |
| 8,313,485 B2 | 11/2012 | Shadduck |
| 8,343,078 B2 | 1/2013 | Toth |
| 8,360,737 B2 | 1/2013 | Smisson, III et al. |
| 8,361,068 B2 | 1/2013 | McClurken |
| 8,366,667 B2 | 2/2013 | Chan et al. |
| 8,372,067 B2 | 2/2013 | Woloszko et al. |
| 8,388,515 B2 | 3/2013 | Shener |
| 8,388,570 B2 | 3/2013 | Kumar et al. |
| 8,388,582 B2 | 3/2013 | Eubanks et al. |
| 8,394,037 B2 | 3/2013 | Toth |
| 8,430,898 B2 | 4/2013 | Wiener et al. |
| 8,444,592 B2 | 5/2013 | Williams et al. |
| 8,447,404 B2 | 5/2013 | Sharma et al. |
| 8,449,500 B2 | 5/2013 | DelCastillo et al. |
| 8,460,178 B2 | 6/2013 | Kumar et al. |
| 8,465,421 B2 | 6/2013 | Finkman et al. |
| 8,491,285 B2 | 7/2013 | Haser et al. |
| 8,512,283 B2 | 8/2013 | Kumar et al. |
| 8,512,326 B2 | 8/2013 | Shadduck et al. |
| 8,535,237 B2 | 9/2013 | Nishtala |
| 8,562,577 B2 | 10/2013 | Michaels et al. |
| 8,568,424 B2 | 10/2013 | Shugrue et al. |
| 8,574,253 B2 | 11/2013 | Gruber et al. |
| 8,591,453 B2 | 11/2013 | Stubkjaer et al. |
| 8,591,464 B2 | 11/2013 | Kumar et al. |
| 8,597,228 B2 | 12/2013 | Pyles et al. |
| 8,620,149 B2 | 12/2013 | Entenman et al. |
| 8,652,089 B2 | 2/2014 | Kumar et al. |
| 8,663,157 B2 | 3/2014 | Hacker et al. |
| 8,663,216 B2 | 3/2014 | Davison et al. |
| 8,728,066 B2 | 5/2014 | Shadduck et al. |
| 8,740,866 B2 | 6/2014 | Reasoner et al. |
| 8,764,408 B2 | 7/2014 | Smisson, III et al. |
| 8,790,303 B2 | 7/2014 | Williams et al. |
| 8,795,232 B2 | 8/2014 | Visconti et al. |
| 8,840,625 B2 | 9/2014 | Adams et al. |
| 8,840,626 B2 | 9/2014 | Adams et al. |
| 8,870,756 B2 | 10/2014 | Maurice |
| 8,870,866 B2 | 10/2014 | Woloszko |
| 8,893,722 B2 | 11/2014 | Emanuel |
| 8,911,363 B2 | 12/2014 | Kumar et al. |
| 8,920,372 B2 | 12/2014 | Faries, Jr. et al. |
| 8,951,274 B2 | 2/2015 | Adams et al. |
| 8,974,448 B2 | 3/2015 | Germain et al. |
| 8,979,798 B2 | 3/2015 | Shener et al. |
| 9,005,157 B2 | 4/2015 | Gerg et al. |
| 9,027,389 B2 | 5/2015 | Abboud et al. |
| 9,028,398 B2 | 5/2015 | Kumar et al. |
| 9,060,800 B1 | 6/2015 | Cesarini et al. |
| 9,072,431 B2 | 7/2015 | Adams et al. |
| 9,078,562 B2 | 7/2015 | Poll et al. |
| 9,084,847 B2 | 7/2015 | Klein et al. |
| 9,089,358 B2 | 7/2015 | Emanuel |
| 9,095,358 B2 | 8/2015 | Woloszko et al. |
| 9,095,366 B2 | 8/2015 | Sullivan et al. |
| 9,101,701 B2 | 8/2015 | Kumar et al. |
| 9,125,550 B2 | 9/2015 | Shener-Irmakoglu et al. |
| 9,144,374 B2 | 9/2015 | Maurice, Jr. |
| 9,173,987 B2 | 11/2015 | Meyer et al. |
| 9,179,821 B2 | 11/2015 | Shener |
| 9,226,650 B2 | 1/2016 | Emanuel |
| 9,226,765 B2 | 1/2016 | Emanuel |
| 9,233,193 B2 | 1/2016 | Truckai et al. |
| 9,248,221 B2 | 2/2016 | Look et al. |
| 9,254,142 B2 | 2/2016 | Germain et al. |
| 9,254,164 B2 | 2/2016 | Woloszko |
| 9,272,086 B2 | 3/2016 | Williams et al. |
| 9,283,045 B2 | 3/2016 | Rhee et al. |
| 9,289,110 B2 | 3/2016 | Woolford et al. |
| 9,289,541 B2 | 3/2016 | Norman et al. |
| 9,427,247 B2 | 8/2016 | Emanuel |
| 9,439,677 B2 | 9/2016 | Germain et al. |
| 9,439,720 B2 | 9/2016 | Germain et al. |
| 9,474,848 B2 | 10/2016 | Williams et al. |
| 9,486,233 B2 | 11/2016 | Bek et al. |
| 9,492,071 B2 | 11/2016 | Woolford et al. |
| 9,498,586 B2 | 11/2016 | Smisson, III et al. |
| 9,511,184 B2 | 12/2016 | Woolford et al. |
| 9,549,754 B2 | 1/2017 | Shadduck et al. |
| 9,561,335 B2 | 2/2017 | Barish et al. |
| 9,595,104 B2 | 3/2017 | Satish et al. |
| 9,597,149 B2 | 3/2017 | Germain et al. |
| 9,597,445 B2 | 3/2017 | Ha et al. |
| 9,603,990 B2 | 3/2017 | Woolford |
| 9,636,170 B2 | 5/2017 | Germain et al. |
| 9,655,557 B2 | 5/2017 | Toth et al. |
| 9,662,060 B2 | 5/2017 | Peliks et al. |
| 9,664,547 B1 | 5/2017 | Koltz, Jr. et al. |
| 9,730,575 B2 | 8/2017 | Shener |
| 9,737,362 B2 | 8/2017 | Germain et al. |
| 9,743,979 B2 | 8/2017 | Germain et al. |
| 9,750,520 B2 | 9/2017 | Emanuel |
| 9,770,541 B2 | 9/2017 | Carr et al. |
| 9,773,320 B2 | 9/2017 | Satish et al. |
| 9,775,542 B2 | 10/2017 | Toth |
| 9,795,433 B2 | 10/2017 | Abboud et al. |
| 9,801,678 B2 | 10/2017 | Cox |
| 9,827,037 B2 | 11/2017 | Germain et al. |
| 9,839,473 B2 | 12/2017 | Germain et al. |
| 9,901,665 B2 | 2/2018 | Klein et al. |
| 9,907,563 B2 | 3/2018 | Germain et al. |
| 9,962,472 B2 | 5/2018 | Woolford et al. |
| 10,077,767 B2 | 9/2018 | Macari et al. |
| 2001/0007925 A1 | 7/2001 | Ritchart et al. |
| 2001/0018550 A1 | 8/2001 | Boebel et al. |
| 2001/0031976 A1 | 10/2001 | Lobdell |
| 2002/0010463 A1 | 1/2002 | Mulier et al. |
| 2002/0038122 A1 | 3/2002 | Peters |
| 2002/0072745 A1 | 6/2002 | Truckai et al. |
| 2002/0085952 A1 | 7/2002 | Ellingboe et al. |
| 2002/0087151 A1 | 7/2002 | Mody et al. |
| 2003/0004470 A1 | 1/2003 | Hickerson et al. |
| 2003/0009164 A1 | 1/2003 | Woloszko et al. |
| 2003/0060862 A1 | 3/2003 | Goble et al. |
| 2003/0097082 A1 | 5/2003 | Purdy et al. |
| 2003/0176833 A1 | 9/2003 | Libermann |
| 2003/0208200 A1 | 11/2003 | Palanker et al. |
| 2003/0212363 A1 | 11/2003 | Shipp |
| 2003/0216689 A1 | 11/2003 | Bouhuijs et al. |
| 2004/0049217 A1 | 3/2004 | Ross et al. |
| 2004/0059363 A1 | 3/2004 | Alvarez et al. |
| 2004/0073175 A1 | 4/2004 | Jacobson et al. |
| 2004/0087888 A1 | 5/2004 | DiGianfilippo et al. |
| 2004/0092980 A1 | 5/2004 | Cesarini et al. |
| 2004/0102770 A1 | 5/2004 | Goble |
| 2004/0167427 A1 | 8/2004 | Quick et al. |
| 2004/0167428 A1 | 8/2004 | Quick et al. |
| 2004/0170409 A1 | 9/2004 | Faries, Jr. et al. |
| 2004/0199226 A1 | 10/2004 | Shadduck |
| 2004/0230190 A1 | 11/2004 | Dahla et al. |
| 2004/0260232 A1 | 12/2004 | Cimino |
| 2004/0267255 A1 | 12/2004 | Auge, II et al. |
| 2005/0096649 A1 | 5/2005 | Adams |
| 2005/0119628 A1 | 6/2005 | Sant et al. |
| 2005/0209507 A1 | 9/2005 | Suzuki et al. |
| 2005/0236329 A1 | 10/2005 | Brotherton et al. |
| 2005/0272975 A1 | 12/2005 | McWeeney et al. |
| 2006/0041186 A1 | 2/2006 | Vancaillie |
| 2006/0047185 A1 | 3/2006 | Shener et al. |
| 2006/0047240 A1 | 3/2006 | Kumar et al. |
| 2006/0100579 A1 | 5/2006 | Maahs et al. |
| 2006/0122556 A1 | 6/2006 | Kumar et al. |
| 2006/0122557 A1 | 6/2006 | Kumar et al. |
| 2006/0129091 A1 | 6/2006 | Bonnette et al. |
| 2006/0135955 A1 | 6/2006 | Shadduck |
| 2006/0178670 A1 | 8/2006 | Woloszko et al. |
| 2006/0200064 A1 | 9/2006 | Gross et al. |
| 2006/0224154 A1 | 10/2006 | Shadduck et al. |

(56) References Cited

U.S. PATENT DOCUMENTS

| | | |
|---|---|---|
| 2006/0253062 A1 | 11/2006 | Liao et al. |
| 2006/0253128 A1 | 11/2006 | Sekine et al. |
| 2007/0016182 A1 | 1/2007 | Lipson et al. |
| 2007/0021713 A1 | 1/2007 | Kumar et al. |
| 2007/0036768 A1 | 2/2007 | Fraser et al. |
| 2007/0045272 A1 | 3/2007 | French et al. |
| 2007/0073098 A1 | 3/2007 | Lenker et al. |
| 2007/0088275 A1 | 4/2007 | Stearns et al. |
| 2007/0123838 A1 | 5/2007 | Bernard et al. |
| 2007/0161978 A1 | 7/2007 | Fedenia et al. |
| 2007/0181499 A1 | 8/2007 | Roberts et al. |
| 2007/0219549 A1 | 9/2007 | Marshall et al. |
| 2007/0244353 A1 | 10/2007 | Larsen |
| 2007/0249990 A1 | 10/2007 | Cosmescu |
| 2007/0265689 A1 | 11/2007 | Frey |
| 2008/0021447 A1 | 1/2008 | Davison et al. |
| 2008/0027368 A1 | 1/2008 | Kollar et al. |
| 2008/0039832 A1 | 2/2008 | Palanker et al. |
| 2008/0051708 A1 | 2/2008 | Kumar et al. |
| 2008/0058588 A1 | 3/2008 | Emanuel |
| 2008/0058842 A1 | 3/2008 | Emanuel |
| 2008/0065060 A1 | 3/2008 | Ein-Gal |
| 2008/0071269 A1 | 3/2008 | Hilario et al. |
| 2008/0091061 A1 | 4/2008 | Kumar et al. |
| 2008/0091071 A1 | 4/2008 | Kumar et al. |
| 2008/0091074 A1 | 4/2008 | Kumar et al. |
| 2008/0095625 A1 | 4/2008 | Honegger et al. |
| 2008/0097468 A1 | 4/2008 | Adams et al. |
| 2008/0097471 A1 | 4/2008 | Adams et al. |
| 2008/0097563 A1 | 4/2008 | Petrie et al. |
| 2008/0103504 A1 | 5/2008 | Schmitz et al. |
| 2008/0154182 A1 | 6/2008 | Martin et al. |
| 2008/0216827 A1 | 9/2008 | Seydel et al. |
| 2008/0232977 A1 | 9/2008 | Pan et al. |
| 2008/0249366 A1 | 10/2008 | Gruber et al. |
| 2008/0249553 A1 | 10/2008 | Gruber et al. |
| 2008/0287893 A1 | 11/2008 | Ineson |
| 2009/0030402 A1 | 1/2009 | Adahan |
| 2009/0043238 A1 | 2/2009 | Lane et al. |
| 2009/0069796 A1 | 3/2009 | Oskin |
| 2009/0082715 A1 | 3/2009 | Charles |
| 2009/0088784 A1 | 4/2009 | DeBoer et al. |
| 2009/0137943 A1 | 5/2009 | Stearns et al. |
| 2009/0157111 A1 | 6/2009 | Goh et al. |
| 2009/0163863 A1 | 6/2009 | Lutwyche |
| 2009/0173943 A1 | 7/2009 | Yu et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2009/0312753 A1 | 12/2009 | Shadduck |
| 2010/0100091 A1 | 4/2010 | Truckai |
| 2010/0121321 A1 | 5/2010 | Ryan |
| 2010/0145325 A1 | 6/2010 | Hoey et al. |
| 2010/0152533 A1 | 6/2010 | Mark |
| 2010/0152656 A1 | 6/2010 | Music |
| 2010/0152724 A1 | 6/2010 | Marion et al. |
| 2010/0152758 A1 | 6/2010 | Mark et al. |
| 2010/0228222 A1 | 9/2010 | Williams et al. |
| 2010/0234797 A1 | 9/2010 | Gelfand et al. |
| 2010/0312054 A1 | 12/2010 | Beyar et al. |
| 2011/0015961 A1 | 1/2011 | Chan |
| 2011/0031191 A1 | 2/2011 | Fukuda et al. |
| 2011/0060273 A1 | 3/2011 | Ofsthun et al. |
| 2011/0150961 A1 | 6/2011 | Perry et al. |
| 2011/0177415 A1 | 7/2011 | Harrington et al. |
| 2011/0213300 A1 | 9/2011 | McWeeney et al. |
| 2011/0224486 A1 | 9/2011 | Nguyen et al. |
| 2011/0264090 A1 | 10/2011 | Shadduck et al. |
| 2011/0270256 A1 | 11/2011 | Nelson et al. |
| 2011/0306968 A1 | 12/2011 | Beckman et al. |
| 2012/0010464 A1 | 1/2012 | Adams et al. |
| 2012/0053583 A1 | 3/2012 | Palanker et al. |
| 2012/0116168 A1 | 5/2012 | Möllstam et al. |
| 2012/0157879 A1 | 6/2012 | Mark et al. |
| 2012/0165725 A1 | 6/2012 | Chomas et al. |
| 2012/0172888 A1 | 7/2012 | Shugrue et al. |
| 2012/0172889 A1 | 7/2012 | Chin et al. |
| 2012/0197280 A1 | 8/2012 | Emanuel |
| 2012/0271110 A1 | 10/2012 | Kumar et al. |
| 2012/0271300 A9 | 10/2012 | Shadduck et al. |
| 2012/0289894 A1 | 11/2012 | Douglas et al. |
| 2012/0330292 A1 | 12/2012 | Shadduck et al. |
| 2013/0046304 A1 | 2/2013 | Germain et al. |
| 2013/0046316 A1 | 2/2013 | Sullivan et al. |
| 2013/0079702 A1 | 3/2013 | Klein et al. |
| 2013/0090642 A1 | 4/2013 | Shadduck et al. |
| 2013/0103021 A1 | 4/2013 | Germain et al. |
| 2013/0172805 A1 | 7/2013 | Truckai et al. |
| 2013/0172870 A1 | 7/2013 | Germain et al. |
| 2013/0211321 A1 | 8/2013 | Dubois et al. |
| 2013/0231652 A1 | 9/2013 | Germain et al. |
| 2013/0245637 A1 | 9/2013 | Norred et al. |
| 2013/0267779 A1 | 10/2013 | Woolford et al. |
| 2013/0296847 A1 | 11/2013 | Germain et al. |
| 2013/0310647 A1 | 11/2013 | Milton et al. |
| 2014/0012097 A1 | 1/2014 | McCrea et al. |
| 2014/0031834 A1 | 1/2014 | Germain et al. |
| 2014/0074136 A1 | 3/2014 | Emanuel |
| 2014/0114238 A1 | 4/2014 | Lee et al. |
| 2014/0114300 A1 | 4/2014 | Orczy-Timko et al. |
| 2014/0303551 A1 | 10/2014 | Germain et al. |
| 2014/0324065 A1 | 10/2014 | Bek et al. |
| 2015/0012023 A1 | 1/2015 | Emanuel |
| 2015/0119795 A1 | 4/2015 | Germain et al. |
| 2015/0157396 A1 | 6/2015 | Germain et al. |
| 2015/0314048 A1 | 11/2015 | Klein et al. |
| 2015/0327752 A1 | 11/2015 | Shener-Irmakoglu et al. |
| 2015/0328379 A1 | 11/2015 | Carr et al. |
| 2016/0022346 A1 | 1/2016 | Shadduck |
| 2016/0081530 A1* | 3/2016 | Imaizumi ............ A61B 1/00009 600/103 |
| 2016/0089184 A1 | 3/2016 | Truckai et al. |
| 2016/0166758 A1 | 6/2016 | Norman et al. |
| 2016/0220102 A1 | 8/2016 | Shener-Irmakoglu et al. |
| 2016/0242844 A1 | 8/2016 | Orczy-Timko |
| 2016/0287779 A1 | 10/2016 | Orczy-Timko et al. |
| 2016/0310666 A1 | 10/2016 | Grim et al. |
| 2017/0000957 A1 | 1/2017 | Carr et al. |
| 2017/0027637 A1 | 2/2017 | Germain et al. |
| 2017/0049952 A1 | 2/2017 | Jezierski et al. |
| 2017/0055810 A1 | 3/2017 | Germain et al. |
| 2017/0120039 A1 | 5/2017 | Childs et al. |
| 2017/0184088 A1 | 6/2017 | Macari et al. |
| 2017/0203028 A1 | 7/2017 | Carr et al. |
| 2017/0296727 A1 | 10/2017 | Burbank et al. |
| 2018/0361055 A1* | 12/2018 | Pereira ............... A61M 3/0254 |
| 2019/0282073 A1 | 9/2019 | Truckai |

FOREIGN PATENT DOCUMENTS

| | | |
|---|---|---|
| EP | 0812574 A2 | 12/1997 |
| EP | 0812574 A3 | 11/1998 |
| EP | 1911391 A1 | 4/2008 |
| EP | 2100567 A1 | 9/2009 |
| GB | 2296869 A | 7/1996 |
| GB | 2327351 A | 1/1999 |
| GB | 2337000 A | 11/1999 |
| JP | 55000199 A | 1/1980 |
| JP | 61185240 A | 8/1986 |
| JP | 1986185240 A | 8/1986 |
| JP | H01213981 A | 8/1989 |
| JP | H04312456 A | 11/1992 |
| JP | 06225851 A | 8/1994 |
| JP | 09084756 A | 3/1997 |
| JP | 2000217908 A | 8/2000 |
| JP | 2002513614 A | 5/2002 |
| JP | 2002529185 A | 9/2002 |
| JP | 2004073833 A | 3/2004 |
| JP | 2004290520 A | 10/2004 |
| JP | 2005529674 A | 10/2005 |
| JP | 2007014854 A | 1/2007 |
| JP | 2008511397 A | 4/2008 |

(56) References Cited

FOREIGN PATENT DOCUMENTS

| JP | 2011212450 A | 10/2011 |
| JP | 2012525915 A | 10/2012 |
| JP | 2014226471 A | 12/2014 |
| WO | 8700759 A1 | 2/1987 |
| WO | 9217040 A1 | 10/1992 |
| WO | 9322979 A1 | 11/1993 |
| WO | 9640331 A1 | 12/1996 |
| WO | 9716220 A1 | 5/1997 |
| WO | 9746271 A1 | 12/1997 |
| WO | 0028890 A1 | 5/2000 |
| WO | 03105697 A1 | 12/2003 |
| WO | 2004043313 A2 | 5/2004 |
| WO | 2005037088 A2 | 4/2005 |
| WO | 2009128435 A1 | 10/2009 |
| WO | 2010096139 A2 | 8/2010 |
| WO | 2010127174 A1 | 11/2010 |
| WO | 2010128994 A1 | 11/2010 |
| WO | 2011060189 A1 | 5/2011 |
| WO | 2010096139 A3 | 12/2011 |
| WO | 2012017959 A1 | 2/2012 |
| WO | 2013003570 A1 | 1/2013 |
| WO | 2013006633 A1 | 1/2013 |
| WO | 2013044243 A1 | 3/2013 |
| WO | 2014168985 A1 | 10/2014 |
| WO | 2018236513 A1 | 12/2018 |

OTHER PUBLICATIONS

Liu et al., "Clinical Application of Hysteriscopic Electroresection in 775 Cases," Di YHi Jun Yi Da Xue Xue Bao. vol. 24(4):467-9, Apr. 2004; (in Chinese with English Abstract).

Phillips et al., "The Effect of Dilute Vasopressin Solution on Blood Loss During Operative Hysteroscopy," J Am Assoc Gynecol Laparosc. vol. 3(4, Supplement):S38, Aug. 1996.

International Search Report and Written Opinion dated Sep. 24, 2012 for PCT/US2012/043892.

International Search Report and Written Opinion dated Oct. 2, 2012 for PCT/US2012/045428.

International search report and written opinion dated Oct. 16, 2012 for PCT/US2012/044609.

International search report and written opinion dated Dec. 4, 2012 for PCT/US2012/056936.

International Search Report and Written Opinion dated May 15, 2013, for PCT/US2013/022559.

International Search Report and Written Opinion dated Feb. 1, 2013 for PCT/US2012/043891.

International Search Report and Written Opinion dated Mar. 13, 2013 for PCT/US2012/063406.

Office Action for U.S. Appl. No. 13/277,913 dated Jan. 29, 2013.

Edmond et al; "Human Ureteral Peristalsis", The Journal of Urology, vol. 104, Nov. 1970.

Miles et al; "Intrarenal Pressure"; Journal of Physiology, vol. 123, pp. 131-142, 1954.

Ross et al; "Observations on the Physiology of the Human Renal Pelvis and Ureter", The Journal of Urology, vol. 97, Mar. 1967.

Weaver et al; "The Relationship of Intrarenal Artery and Renal Intrapelvic Pressure", The Journal of Urology, vol. 101, Jun. 1969.

International Search Report and Written Opinion dated Sep. 7, 2020 for International Application No. PCT/US2020/039504.

* cited by examiner

DETECTION OF AN ENDOSCOPE TO A FLUID MANAGEMENT SYSTEM

CROSS-REFERENCE TO RELATED APPLICATIONS

This application claims the benefit of priority of U.S. Provisional Application No. 62/867,557 filed Jun. 27, 2019, the entire disclosure of which is hereby incorporated by reference.

TECHNICAL FIELD

The disclosure is directed to a fluid management system. More particularly, the disclosure is directed to a system and method for verifying connectivity of a device to a fluid management system.

BACKGROUND

Flexible ureteroscopy (fURS), gynecology, and other endoscopic procedures require the circulation of fluid for several reasons. Surgeons today deliver the fluid in various ways such as, for example, by hanging a fluid bag and using gravity to deliver the fluid, filling a syringe and manually injecting the fluid or using a peristaltic pump to deliver fluid from a reservoir at a fixed pressure or flow rate via a fluid management system. Fluid management systems may adjust the flow rate and/or pressure at which fluid is delivered from the reservoir based on data collected from a procedural device, such as, but not limited to, an endoscope. Of the known medical devices, systems, and methods, each has certain advantages and disadvantages. There is an ongoing need to provide alternative medical devices and fluid delivery systems.

SUMMARY

The disclosure is directed to systems and methods for verifying connectivity of a procedural device to a fluid management system.

In a first example, a fluid management and medical device system may comprise a fluid management system and a medical device. The fluid management system may comprise a pump configured to pump fluid from a fluid supply source through the fluid management system at a fluid flow rate and a processing device including a user interface, the processing device configured to control the pump to maintain a target fluid flow rate based on the set of system operating parameters. The medical device may comprise an elongate shaft in fluid communication with the pump of the fluid management system, a pressure sensor disposed at a distal end of the elongate shaft, and a handle coupled to a proximal end of the elongate shaft. The processing device of the fluid management system may be configured to adjust the fluid flow rate based on data received from the pressure sensor of the medical device and the processing device of the fluid management system may be configured to verify the medical device is in a patient's body prior to adjusting the fluid flow rate based on the data received from the pressure sensor of the medical device.

Alternatively or additionally to any of the examples above, in another example, the processing device of the fluid management system may be configured to compare a pulsatile pressure generated at the pump with the data received from the pressure sensor of the medical device.

Alternatively or additionally to any of the examples above, in another example, the pulsatile pressure generated at the pump and the data received from the pressure sensor of the medical device may each be filtered, normalized, and converted to a frequency domain.

Alternatively or additionally to any of the examples above, in another example, when a dominant tone extracted from the frequency domain of the pulsatile pressure generated at the pump matches a dominant tone extracted from the frequency domain of the data received from the pressure sensor, the processing device of the fluid management system may determine the medical device is in use within the patient's body.

Alternatively or additionally to any of the examples above, in another example, the system may further comprise a temperature sensor disposed at the distal end of the elongate shaft of the medical device.

Alternatively or additionally to any of the examples above, in another example, when a temperature measured at the temperature sensor is greater than a threshold temperature above room temperature, the processing device of the fluid management system may determine the medical device is in use within the patient's body. In some instances, the threshold temperature may be 25° C., 28° C., 30° C., 32° C., or 35° C.

Alternatively or additionally to any of the examples above, in another example, the system may further comprise a stress sensor disposed at the distal end of the elongate shaft of the medical device.

Alternatively or additionally to any of the examples above, in another example, when a stress measured at the stress sensor is above a predetermined threshold, the processing device of the fluid management system may determine the medical device is in use within the patient's body.

Alternatively or additionally to any of the examples above, in another example, the stress sensor may be a Fiber Bragg grating optical fiber.

Alternatively or additionally to any of the examples above, in another example, the system may further comprise a position marker at the distal end of the elongate shaft of the medical device, the position marker configured for use in sensing in a magnetic field of a mapping and navigation system.

Alternatively or additionally to any of the examples above, in another example, a position of the position marker may be determined relative to the patient.

Alternatively or additionally to any of the examples above, in another example, when the position of the position marker is within the patient's body, the processing device of the fluid management system may determine the medical device may be in use within the patient's body.

Alternatively or additionally to any of the examples above, in another example, the processing device of the fluid management system may be configured to compare a pulsatile pressure generated within the body with the data received from the pressure sensor of the medical device, and when the data received from the pressure sensor of the medical device matches the pulsatile pressure the processing device of the fluid management system may determine the medical device is in use within the patient's body.

Alternatively or additionally to any of the examples above, in another example, the processing device of the fluid management system may be configured to compare an atmospheric pressure with the data received from the pressure sensor of the medical device while the pump is active, and when the data received from the pressure sensor of the medical device is greater than the atmospheric pressure the processing device of the fluid management system may determine the medical device is in use within the patient's body.

Alternatively or additionally to any of the examples above, in another example, the medical device may further comprise a workstation in electronic communication with the pressure sensor and the processing device of the fluid management system, the workstation including at least a display and a processor.

In another example, a fluid management and medical device system may comprise a fluid management system and a medical device. The fluid management system may comprise a pump configured to pump fluid from a fluid supply source through the fluid management system at a fluid flow rate and a processing device including a user interface, the processing device configured to control the pump to maintain a target fluid flow rate based on the set of system operating parameters. The medical device may comprise an elongate shaft in fluid communication with the pump of the fluid management system, and a pressure sensor disposed at a distal end of the elongate shaft, a handle coupled to a proximal end of the elongate shaft. The processing device of the fluid management system may be configured to adjust the fluid flow rate based on data received from the pressure sensor of the medical device and the processing device of the fluid management system may be configured to verify the medical device is in a patient's body prior to adjusting the fluid flow rate based on the data received from the pressure sensor of the medical device.

Alternatively or additionally to any of the examples above, in another example, the processing device of the fluid management system may be configured to compare a pulsatile pressure generated at the pump with the data received from the pressure sensor of the medical device and the pulsatile pressure generated at the pump and the data received from the pressure sensor of the medical device may each be filtered, normalized, and converted to a frequency domain.

Alternatively or additionally to any of the examples above, in another example, when a dominant tone extracted from the frequency domain of the pulsatile pressure generated at the pump matches a dominant tone extracted from the frequency domain of the data received from the pressure sensor, the processing device of the fluid management system may determine the medical device is in use within the patient's body.

Alternatively or additionally to any of the examples above, in another example, the system may further comprise a temperature sensor disposed at the distal end of the elongate shaft of the medical device and when a temperature measured at the temperature sensor is above room temperature, the processing device of the fluid management system may determine the medical device is in use within the patient's body.

Alternatively or additionally to any of the examples above, in another example, the system may further comprise a stress sensor disposed at the distal end of the elongate shaft of the medical device and when a stress measured with the stress sensor is above a predetermined threshold, the processing device of the fluid management system may determine the medical device is in use within the patient's body.

Alternatively or additionally to any of the examples above, in another example, the medical device may further comprise a workstation in electronic communication with the pressure sensor and the processing device of the fluid management system, the workstation including at least a display and a processor.

Alternatively or additionally to any of the examples above, in another example, the system may further comprise a position marker at the distal end of the elongate shaft of the medical device, the position marker configured for use in sensing in a magnetic field of a mapping and navigation system and a position of the position marker may be determined relative to the patient.

Alternatively or additionally to any of the examples above, in another example, when the position of the position marker is within the patient's body, the processing device of the fluid management system may determine the medical device is in use within the patient's body.

Alternatively or additionally to any of the examples above, in another example, the processing device of the fluid management system may be configured to compare a pulsatile pressure generated within the body with the data received from the pressure sensor of the medical device, and when a characteristic extracted from the data received from the pressure sensor of the medical device matches a characteristic extracted the pulsatile pressure, the processing device of the fluid management system may determine the medical device is in use within the patient's body.

Alternatively or additionally to any of the examples above, in another example, the processing device of the fluid management system may be configured to compare an atmospheric pressure with the data received from the pressure sensor of the medical device while the pump is active, and when the data received from the pressure sensor of the medical device is greater than the atmospheric pressure, the processing device of the fluid management system may determine the medical device is in use within the patient's body.

In another example, a fluid management and medical device system may comprise a fluid management system and a medical device. The fluid management system may comprise a pump configured to pump fluid from a fluid supply source through the fluid management system at a fluid flow rate and a processing device including a user interface, the processing device configured to control the pump to maintain a target fluid flow rate based on the set of system operating parameters. The medical device may comprise an elongate shaft in fluid communication with the pump of the fluid management system, a pressure sensor disposed at a distal end of the elongate shaft, and a handle coupled to a proximal end of the elongate shaft. The processing device of the fluid management system may be configured to adjust the fluid flow rate based on data received from the pressure sensor of the medical device and the processing device of the fluid management system may be configured to verify the medical device is in a patient's body using at least a first verification process and a second verification process prior to adjusting the fluid flow rate based on the data received from the pressure sensor of the medical device.

Alternatively or additionally to any of the examples above, in another example, the processing device may be further configured to use a third verification process prior to adjusting the fluid flow rate based on the data received from the pressure sensor of the medical device.

Alternatively or additionally to any of the examples above, in another example, each of the first verification process, the second verification process, and the third verification process may be different.

Alternatively or additionally to any of the examples above, in another example, if a majority of the first, second, and third verification processes indicate the medical device is in a patient's body, the processing device of the fluid management system may determine the medical device is in use within the patient's body.

Alternatively or additionally to any of the examples above, in another example, the processing device of the fluid management system may be configured to use a weighted average of a result from each of the first, second, and third verification processes to determine if the medical device is in use within the patient's body.

In another example, a method for verifying a medical device is in use may comprise receiving a first set of data from a medical device, receiving a second set of data from a fluid management system, the second set of data being a same type of data as the first set of data, comparing the first set of data with the second set of data, and if the first set of data and the second set of data meet a predetermined condition, determining the medical device is within a body of a patient.

Alternatively or additionally to any of the examples above, in another example, the first set of data may be one or more pressure readings obtained at a distal end of the medical device and the second set of data may be one or more pressure readings obtained at the fluid management system and the first set of data and the second set of data may each be filtered, normalized, and converted to a frequency domain.

Alternatively or additionally to any of the examples above, in another example, the first set of data and the second set of data may meet the predetermined condition when a dominant tone extracted from the frequency domain of the first set of data and a dominant tone extracted from the second set of data match.

Alternatively or additionally to any of the examples above, in another example, the first set of data may be one or more temperature readings obtained at a distal end of the medical device and the second set of data may be an ambient temperature and the first set of data and the second set of data may meet the predetermined condition when the one or more temperature readings of the first set of data is greater than the ambient temperature.

Alternatively or additionally to any of the examples above, in another example, the first set of data may be one or more pressure readings obtained at a distal end of the medical device while the fluid management system is active and the second set of data may be an atmospheric pressure and the first set of data and the second set of data may meet the predetermined condition when the one or more pressure readings of the first set of data is greater than the atmospheric pressure.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
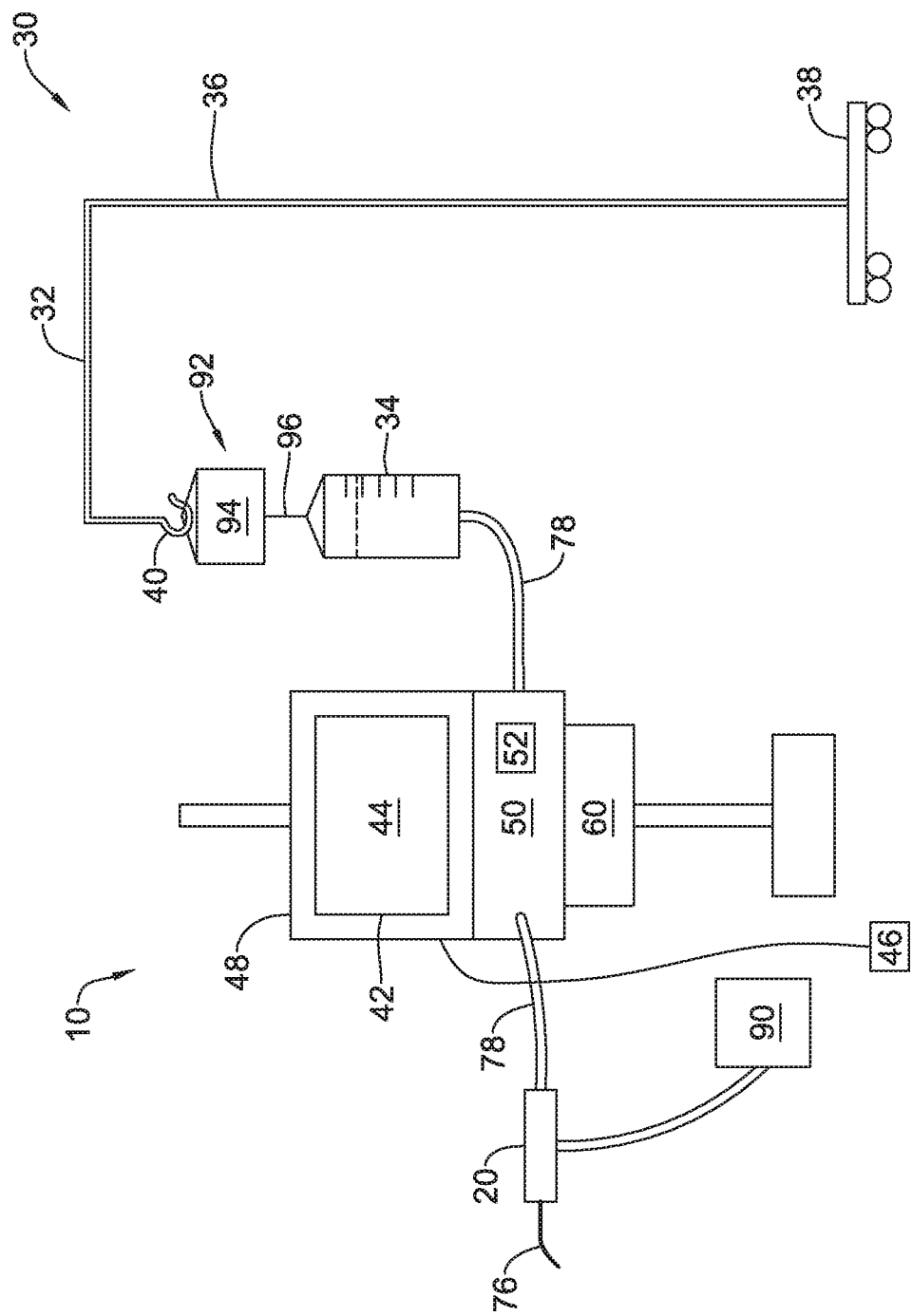
FIG. 1 is a schematic illustration of a fluid management system according to an illustrative embodiment of the present disclosure.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The terms "proximal" and "distal" as used herein are intended to refer to a direction toward (proximal) and away from (distal) a user of the device.

Some fluid management systems for use in flexible ureteroscopy (fURS) procedures (e.g., ureteroscopy, percutaneous nephrolithotomy (PCNL), benign prostatic hyperplasia (BPH), etc.), gynecology, and other endoscopic procedures may regulate body cavity pressure when used in conjunction with an endoscope device such as, but not limited to, a LithoVue™ scope device using pressure and/or temperature data from the endoscope or other endoscopic device. Direct regulation of the intracavity pressure during a medical procedure may allow the fluid management system to safely drive system pressures of up to 600 mmHg to ensure no loss of flow during the procedure when tools are inserted into the working channel of the endoscope device. However, the fluid management system may need to determine when it is safe to use the endoscope data for regulating body cavity pressure (e.g., intrarenal pressure). Systems and methods for verifying the endoscope device is connected to the fluid management system and in use within the body are desired.

FIG. 1 is a schematic view of an illustrative fluid management system 10 that may be used in an endoscopic procedure, such as fURS procedures. The fluid management system 10 may be coupled to a surgical device 20 that allows flow of fluid therethrough and includes a pressure sensor. An illustrative surgical device may be a LithoVue' scope device, or other endoscope. In an illustrative embodiment, the device 20 may include a temperature sensor to provide intracavity temperature feedback to the fluid management system 10, a pressure sensor to provide intracavity pressure feedback to the fluid management system 10, and/or a camera to provide visual feedback to the fluid management system 10.

Briefly, the fluid management system 10 may include a pump system 50 configured to transfer fluid from a fluid bag 34 to the medical device 20. In some cases, the fluid may pass through a heating system 60 prior to entering the medical device 20. The flow of fluid, pressure of the fluid, temperature of the fluid, and other operational parameters may be controlled by or at least partially controlled by a main processing device 48 including a display screen 44. The main processing device 48 may be in electronic communication (e.g., wired or wireless) with the medical device 20, the pump system 50, and/or the heating system 60 to provide control commands and/or to transfer or receive data therebetween. For example, as will be described in more detail herein, the main processing system 48 may receive data from the medical device 20, such as, but not limited to, pressure and temperature data. The main processing system 48 may then use the data received from the medical device 20 to control operational parameters of the pump system 50 and/or the heating system 60.

The fluid management system 10 also includes a fluid management unit 30. An illustrative fluid management unit 30 may include one or more fluid container supports, such as fluid bag hangers 32, each of which supports one or more fluid bags 34. In an embodiment, placement of the fluid bag 34 may be detected using a remote sensor. The fluid bag hangers 32 may receive a variety of sizes of fluid bags 34 such as, for example, 1 liter (L) to 5 L bags. It will be understood that any number of fluid containers may be used. Furthermore, fluid containers of any size may be used depending on the procedure. An illustrative fluid management unit 30 may be mounted to a rolling stand, which may include a pole 36 and/or a base 38. The base 38 may include a plurality of wheels to facilitate easy movement of the fluid management unit 30 when in use. However, it will be understood that the fluid bag 34 may also be hung from the ceiling or other location depending on the clinical preference. The fluid bag hanger 32 extends from the pole 36 and may include one or more hooks 40 from which one or more fluid bags 34 may be suspended. The fluid used in the fluid management unit 30 may be 0.9% saline. However, it will be understood that a variety of other fluids of varying viscosities may be used depending on the procedure.

The fluid management system 10 may also include one or more user interface components such as a touch screen interface 42. The touch screen interface 42 includes a display screen 44 and may include switches or knobs in addition to touch capabilities. The touch screen interface 42 allows the user to input/adjust various functions of the system 10 such as, for example flow rate, pressure or temperature. The user may also configure parameters and alarms (such as, but not limited to, a max pressure alarm), information to be displayed, and the procedure mode. The touch screen interface 42 allows the user to add, change or discontinue the use of various modular systems within the fluid management system 10. The touch screen interface 42 may also be used to change the system 10 between automatic and manual modes for various procedures. It is contemplated that other systems configured to receive user input may be used in place of or in addition to the touch screen interface 42.

The touch screen interface 42 may be configured to include selectable areas like buttons and/or may provide a functionality similar to physical buttons as would be understood by those skilled in the art. The display screen 44 may be configured to show icons related to modular systems and devices included in the fluid management system 10. For example, the display screen 44 may provide the user with a live video feed of the target tissue/vessel/cavity from the scope or medical device 20. The display screen 44 may also include a flow rate display. The flow rate display may be determined based on a desired threshold for flow rate set by the user prior to the procedure or based on known common values, etc. In some embodiments, the operating parameters may be adjusted by touching the corresponding portion of the touch screen interface 42. The touch screen interface 42 may also display visual alerts and/or audio alarms if parameters (e.g., flow rate, temperature, etc.) are above or below predetermined thresholds. The touch screen interface 42 may also be configured to display the system power, the amount of fluid remaining in the fluid bag 34, and any other information the user may find useful during the procedure. In an illustrative embodiment, the fluid management system 10 may also include further user interface components such as a foot pedal 46, a heater user interface, a fluid control interface or other device to manually control various modular systems. For example, the foot pedal 46 may be used to manually control flow rate. Some illustrative display screens 44 and other user interface components are described in described in commonly assigned U.S. Patent Publication Number 2018/0361055, titled AUTOMATED FLUID MANAGEMENT SYSTEM, the disclosure of which is hereby incorporated by reference.

The touch screen interface 42 may be operatively connected to or a part of the main processing device 48. The main processing device 48 may be a computer, tablet computer, or other processing device. The main processing device 48 may be operatively connected to one or more system components such as, for example, the pump system 50, the heating system 60 and a fluid deficit management system. The main processing device 48 is capable of and configured to perform various functions such as calculation, control, computation, display, etc. The main processing device 48 is also capable of tracking and storing data pertaining to the operations of the management system 10 and each component thereof. In an illustrative embodiment, the main processing device 48 includes network communication capabilities, such as Wi-Fi, through which the processing device 48 may be connected to, for example, a local area network. The main processing device 48 may also receive signals from the sensors of the system 10. In an embodiment, the main processing device 48 may communicate with databases for best practice suggestions and the maintenance of patient records which may be displayed to the user on the display screen 44.

The fluid management system 10 may be user selectable between different modes based on the procedure, patient characteristics, etc. For example, different modes may include, but are not limited to, fURS Mode, BPH Mode, Hysteroscopy Mode, Cystoscopy Mode, etc. Once a mode has been selected by the user, mode parameters such as flow rate, pressure, fluid deficit and temperature are provided to the user via the display screen. The exemplary parameters of the specific modes may be previously determined and loaded onto the main processing device 48 using, for example, software. Thus, when a user selects a procedure from an initial display on the touch screen interface display screen 44, these known parameters are loaded from the processor to the various components of the fluid management system 10, such as, but not limited to the pump system 50, the heating system 60, the fluid deficit management system, etc. The fluid management system 10 may also be user selectable between automatic and manual mode. For example, for certain procedures, the user may wish to manually adjust a flow rate, pressure or other parameters. Once the user has selected the manual mode on, for example, the touch screen interface 42, the user may the adjust flow rate or pressure via other manual interfaces such as the foot pedal 46 or the fluid control interface. If the user selects an automatic mode, the user may be prompted to select or input via the touch screen interface 42 which medical device 20 is being used so that the processing device 48 may determine if data obtained from the medical device 20 can be used to facilitate control of the fluid management system 10. As will be described in more detail herein, the fluid management system 10 may be configured to verify the medical device 20 selected is actually being used prior to using the collected data.

The main processing device 48 may be configured to include visual software/image recognition software that can detect visual noise based on variations in brightness (e.g., light monitoring), contrast, or color pixilation. If the image provided to the main processing device 48 is determined to be not sufficiently clear or sharp, the fluid management system 10 increases the flow rate of the fluid to flush out debris to sharpen/clear the image. The flow rate is increased for a temporary time (e.g., a predetermined time period) or until the field of view is deemed to be sufficiently clear. This temporary increase ensures that the time at which a flow rate is increased is limited to ensure that pressure does not exceed safe limits. For example, the system 10 may recognize a red hue in the irrigation (a sign of blood) and signal to one or more peristaltic pumps 52 within the pump assembly 50 to increase the flow rate until the blood is cleared from the field of view. Alternatively, the processing device 48 may provide a visual alert on the display screen 44 or an audible alert to the physician or nurse that a cloudy view has been detected and the user may then adjust the irrigation flow rate manually. In another example, in instances where there is a lot of debris, light reflected from the debris will brighten the image substantially. In this situation, the main processing device 48 detects this inordinate brightness and signals to the pump system 50 to increase a flow rate to remove debris. Once the reflected light has been reduced as the debris is flushed clear of the field of view of the vision system, the pump system 50 is controlled by the main processing device 48 to reduce the flow rate. In some cases, the physician may create a baseline level for visibility at which he or she prefers to initiate a field clearing flow of fluid and input these parameters into the system 10 via the touch screen interface 42 prior to the procedure. Once the baseline has been created, the system 10 monitors the visual feed for variation in the picture and adjusts the flow rate as necessary.

In order to adjust the rate of flow of fluid through the system 10, the fluid management unit 30 may include one or more pressurization devices such as a pump 52. An illustrative pump 52 may be a peristaltic pump. The pump 52 may be electrically driven and may receive power from a line source such as a wall outlet or an external or internal electrical storage device such as a disposable or rechargeable battery. The peristaltic pump 52 may operate at any desired speed sufficient to deliver fluid at a target pressure such as, for example, 5 mmHg to 50 mmHg. As noted previously, the pump 52 may be automatically adjusted based on, for example, pressure and temperature readings within the patient and/or visual feedback from the medical device 20. The pump 52 may also be manually adjusted via, for example, foot pedal 46, the touch screen interface 42, or a separate fluid controller. While not explicitly shown, the fluid controller may be a separate user interface including buttons that allow the user to increase or decrease each individual pump 52. Alternatively, the fluid controller may be incorporated into the main processing device and receive input via the touch screen interface 42. It will be understood that any number of pumps may be used. In an embodiment, the fluid management system 10 may include multiple pumps having different flow capabilities. A flow meter may be located before and/or after the pump(s) 52.

The flow rate of the fluid at any given time is displayed on the display screen 44 to allow the operating room (OR) visibility for any changes. If the OR personnel notice a change in flow rate that is either too high or too low, the user may manually adjust the flow rate back to a preferred level. This may happen, for example, as physicians insert and remove tools into the working channel of the medical device 20. The fluid management system 10 may also monitor and automatically adjust the flow rate based on previously set parameters, as previously discussed. This feature may also be beneficial when flow is provided manually such as an assistant injecting irrigation through a syringe.

As noted above, in an embodiment, the fluid management system 10 may include visual software or image recognition and analysis software. In this embodiment, the fluid management system 10 may detect, via a camera 70 (see, for example, FIGS. 2 and 3) positioned on the medical device 20 within the body, whether a tool has been inserted or not and which tool is being used. The tool may, for example, have an identifiable marker that the visual software may see to inform the system what type of tool is being used. The fluid management system 10 may then automatically adjust the flow rate based on the tool identified by the visual software. When the tool is retracted from the working channel, the fluid management system 10 reduces the pump rate accordingly.

Additionally, or alternatively, the fluid management system 10 may automatically adjust the flow rate based on a pressure and/or a temperature detected within the patient. The pressure and/or the temperature may be measured in line through a tool, such as temperature sensors 72 and/or pressure sensors or transducers 74 mounted on the medical device 20, used in conjunction with the fluid management system 10. The fluid management system 10 may include pressure monitoring software so that the pump 52 may be configured by the user to be automatically started, stopped, and/or speed adjusted by the fluid management system 10 to maintain a fluid pressure delivered to a surgical site at a target pressure and/or within a predetermined pressure band. For example, a scope pressure sensor 74 may detect pressure within the kidney and automatically alter the flow rate within the fluid management system 10 based on a monitored intrarenal pressure. If intrarenal pressure is too high, the fluid management system 10 will decrease the flow rate and vice versa. In an exemplary temperature control mode, the fluid management system 10 may include temperature monitoring software so that the heating system 60 may be controlled (e.g., started, stopped, and temperature adjusted) to maintain a fluid temperature delivered to a surgical site at about a target temperature and/or within a predetermined temperature pressure band, as will be described in further detail below. For example, the temperature may be monitored in vivo or in vitro and the flow of fluid altered based on the temperature feedback provided. In an illustrative embodiment, the fluid management system 10 may compare the temperature and pressure sensed within the kidney to known values and provide a warning when the parameters are outside of a predetermined safe region. The warning may be a visual or audio alert.

In an embodiment, the fluid management system 10 may monitor movement of a target structure such as, for example, a kidney stone. The fluid management system 10 may calculate the rate of movement based on the original position of the stone and its new position. If the movement exceeds a predetermined threshold, the user may be alerted to manually adjust the flow rate of the fluid management system 10. As described above, flow rate may be adjusted manually via a foot pedal 46, the touch screen interface 42 and/or a pump interface. In an embodiment, if the fluid management system 10 is in an auto mode, the fluid management system 10 will automatically adjust the flow of irrigation as necessary automatically. This capability may be extremely beneficial during procedures such as a lithotripsy to control retropulsion of the stone.

Figure 2:
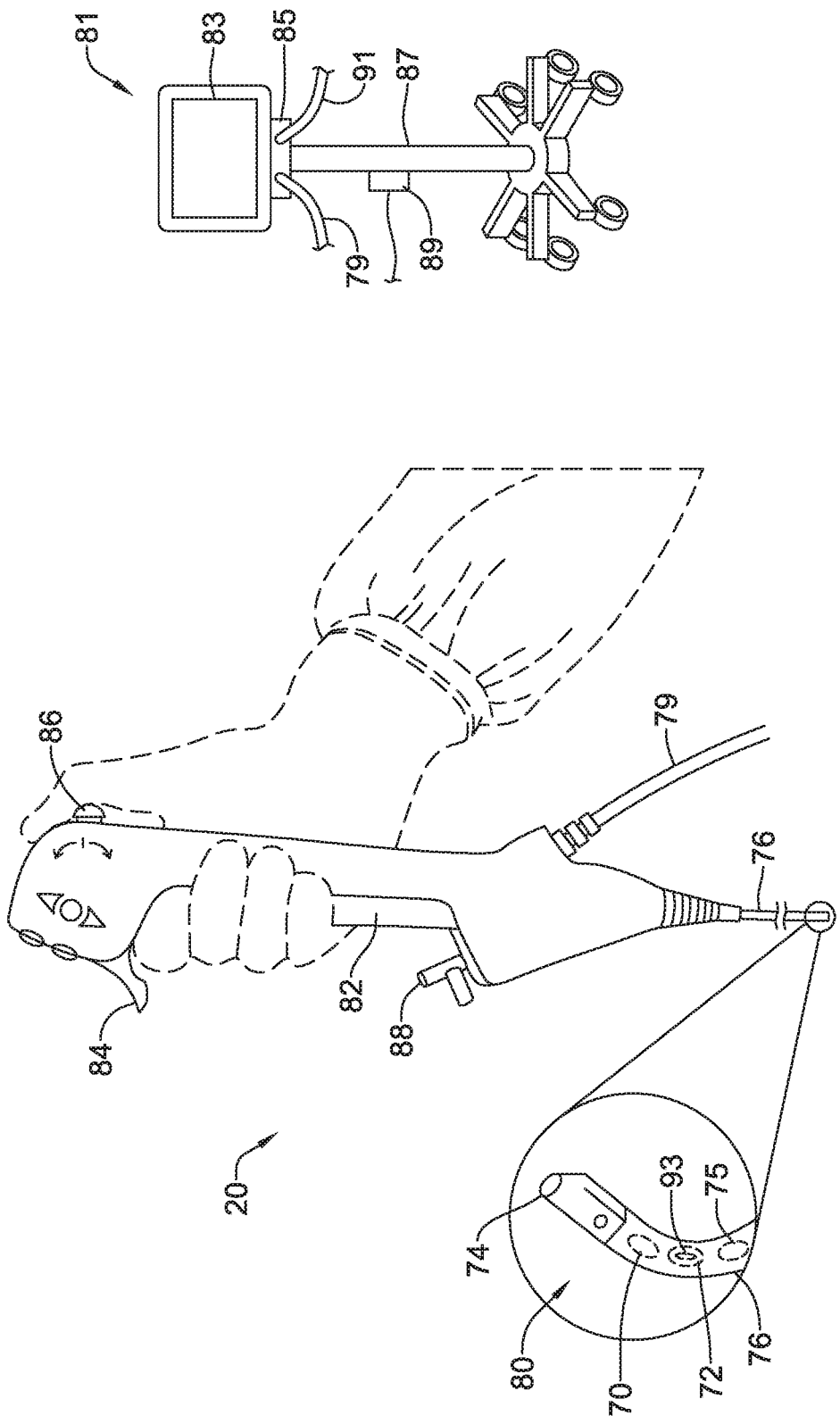
FIG. 2 is a side view of a medical device of the system of FIG. 1 according to an illustrative embodiment.
Figure 3:
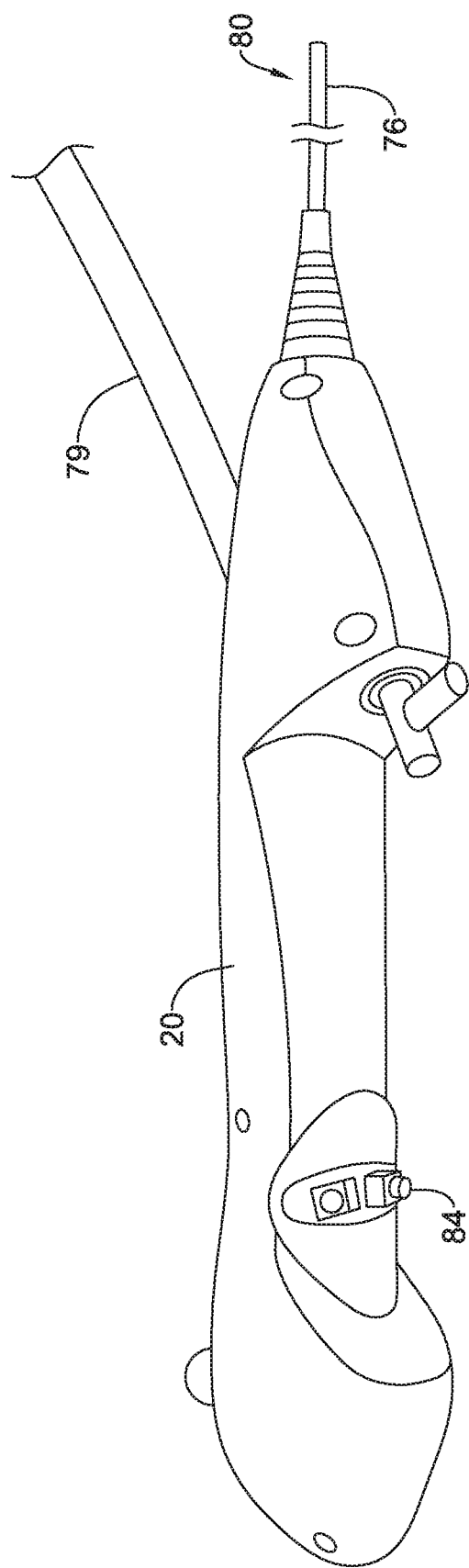
FIG. 3 is a top view of the medical device of FIG. 2.
Figure 4:
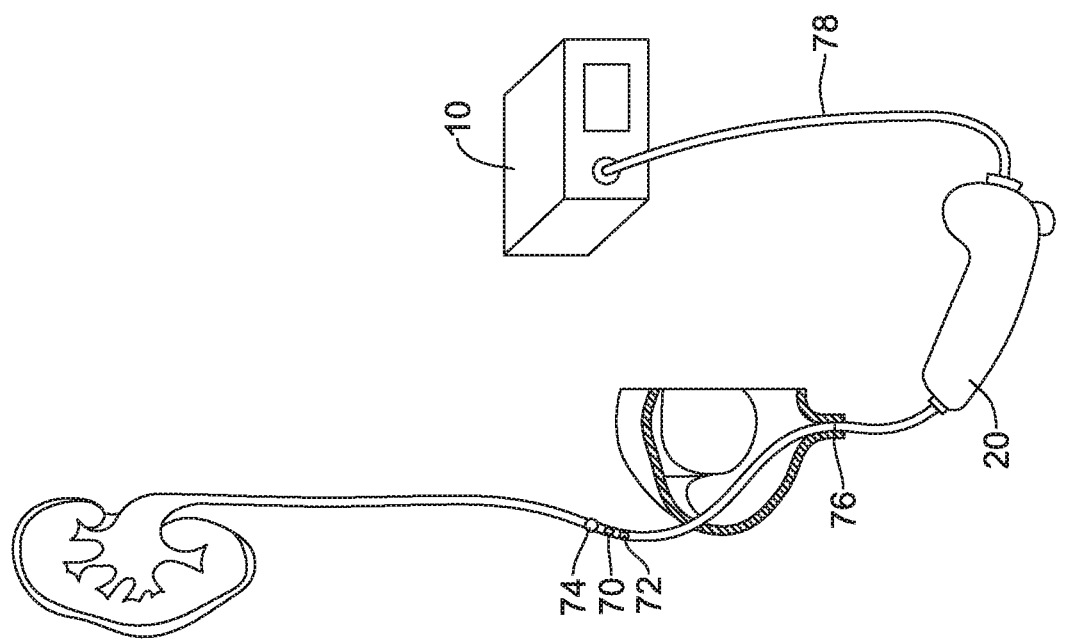
FIG. 4 is a schematic illustration of the medical device of FIG. 2 in situ.

FIGS. 2 and 3 are schematic views of an illustrative medical device 20 that may be used in conjunction with the fluid management system 10. In the illustrated embodiments, the medical device 20 may be a ureteroscope such as a LithoVue™ scope. However, other medical devices, such as another endoscope, may be used in addition to or in place of a ureteroscope. The medical device 20 delivers fluid from the fluid management system 10 to the target tissue via an elongate or scope shaft 76. The elongate shaft 76 may include one or more working lumens for receiving a flow of fluid or other medical devices therethrough. The medical device 20 is connected to the fluid management system 10 via one or more supply line(s) 78 (e.g., a tube), as shown in FIG. 4, which is a schematic view of the medical device 20 in fluid communication with the fluid management system 10 and positioned within a patient's body.

The medical device 20 may be in electronic communication with a workstation 81 via a wired connection 79. The workstation 81 may include a touch panel computer 83, an interface box 85 for receiving the wired connection 79, a cart 87, and a power supply 89, among other features. In some cases, the interface box 85 may be configured to be in wired or wireless communication 91 with the main processing device 48. The touch panel computer 83 may include at least a display screen, an image processor, and a controller. In some cases, the workstation 81 may be a multi-use component (e.g., used for more than one procedure) while the medical device 20 may be a single use device, although this is not required. In some cases, the workstation 81 may be omitted and the medical device 20 may be directly coupled to the main processing device 48 of the fluid management system.

The supply line(s) 78 from the fluid management system 10 to the medical device 20 may be formed of a material the helps dampen the peristaltic motion created by the pump(s) 52. As shown in FIG. 2, the medical device 20 may include a pressure transducer 74 at a distal tip of the scope shaft 76 to measure pressure within, for example, the kidney. The medical device 20 may also include other sensors such as, for example, a temperature sensor 72, a Fiber Bragg grating optical fiber 75 to detect stresses, and/or an antenna or electromagnetic sensor 93. In an illustrative embodiment, the distal end 80 of the medical device 20 may also include at least one camera 70 to provide a visual feed to the user on the display screen 44. In another embodiment, the medical device 20 may include two cameras 70 having different communications requirements or protocols so that different information may be relayed to the user by each camera 70. When so provided, the user may switch back and forth between cameras 70 at will through the touch screen interface 42. While not explicitly shown, the scope shaft 76 may include one or more working lumens for receiving the fluid and/or other medical devices.

The medical device 20 includes a handle 82 coupled to a proximal end of the elongate shaft 76. The handle 82 may have a fluid flow on/off switch 84, which allows the user to control when fluid is flowing through the medical device 20 and into the patient. The handle 82 may further include other buttons 86 that perform other various functions. For example, in one embodiment, the scope handle 82 may include buttons to control the temperature of the scope or fluid. In another embodiment, the scope handle 82 may include a laser so that the user may fire laser energy. In an illustrative embodiment, the laser may be a Lumenis or StarMed Tech Laser. A laser fiber may be connected to the laser system and inserted through the ureteroscope working channel. The user may fire the laser so that energy comes out of the laser fiber tip which hits the debris/stone to break it up. In an exemplary embodiment including a laser button on the scope, a communication line between the laser system and the scope is maintained (e.g., hardwire or wireless). It will be understood that while the exemplary embodiment describes a ureteroscope, the features detailed above may also be directly integrated into a cystoscope, hysteroscope, or virtually any device with an image capability. Medical device 20 may also include a drainage port 88 which may be connected to a drainage system 90. Some illustrative drainage systems 90 are described in described in commonly assigned U.S. Patent Publication Number 2018/0361055, titled AUTOMATED FLUID MANAGEMENT SYSTEM, the disclosure of which is hereby incorporated by reference.

Returning briefly to FIG. 1, the fluid management system 10 may include a fluid deficit monitoring system 92. In an illustrative embodiment, the fluid deficit monitoring system 92 monitors the amount of fluid (e.g., saline) in a fluid bag 34 through weight. For example, a weight sensor 94 such as a scale is hung from the hook 40. The weight sensor 94 may also include a hook 96 from which one or more fluid bags 34 are suspended. The weight sensor 94 determines a weight of the fluid bag 34 attached to the management unit 30 to compare an initial amount of fluid in the fluid bag 34 to a current amount of fluid remaining in the fluid bag 34. The readout of the scale is shown to the user on the display screen 44. As the procedure proceeds, the readout of the scale is updated in real time to alert the physician to how much fluid is left in the fluid bag 34 and this amount may then be used to determine the amount of fluid that has been infused into the patient. In an illustrative embodiment, the fluid management system 10 provides the amount of time remaining before a new bag is needed based on the weight of the bag 34 and the rate at which the bag 34 is emptying (e.g., flow rate). In another embodiment, the amount of fluid remaining may be shown. An alert may be shown on the display screen 44 with an audible signal when, for example, 10% of the saline is left in the bag 34. In an illustrative embodiment, the weight sensor 94 may connect to the display screen 44 via a Wi-Fi signal. In another exemplary embodiment, the weight sensor 94 may be connected to the display screen 44 via a hard wire connection.

In another illustrative embodiment, the fluid deficit monitoring system 92 may include a pressure sensor connected inline between the fluid bag 34 and the device 20. In this embodiment, pressure is determined based on the height of the fluid bag 34. The amount of head pressure decreases as the bag empties. When the pressure falls below a threshold set by the user, an alert is shown on the display screen 44 and an audible signal is emitted. In another exemplary embodiment, the fluid deficit monitoring system 92 may be set to a specific flow rate based on the amount of time that has passed. The physician may enter a bag fluid volume into the fluid management system 10 which then calculates the amount of fluid already used and how much is left based on the known flow rate and the amount of time the fluid management system 10 has been in use.

The fluid management system 10 may utilize small diameter pump tubing 78 to connect various components. Illustrative tubing 78 for irrigation procedures may be less than or equal to 1/16 inches in diameter. However, it will be understood that tubing size may vary based on the application. Tubing may be disposable and provided sterile and ready to use. Different types of tubing may be used for various functions within the fluid management system 10. For example, one type of tubing may be used for fluid heating and fluid flow control to the device 20 while another type of tubing may be used for irrigation within the body.

Figure 5:
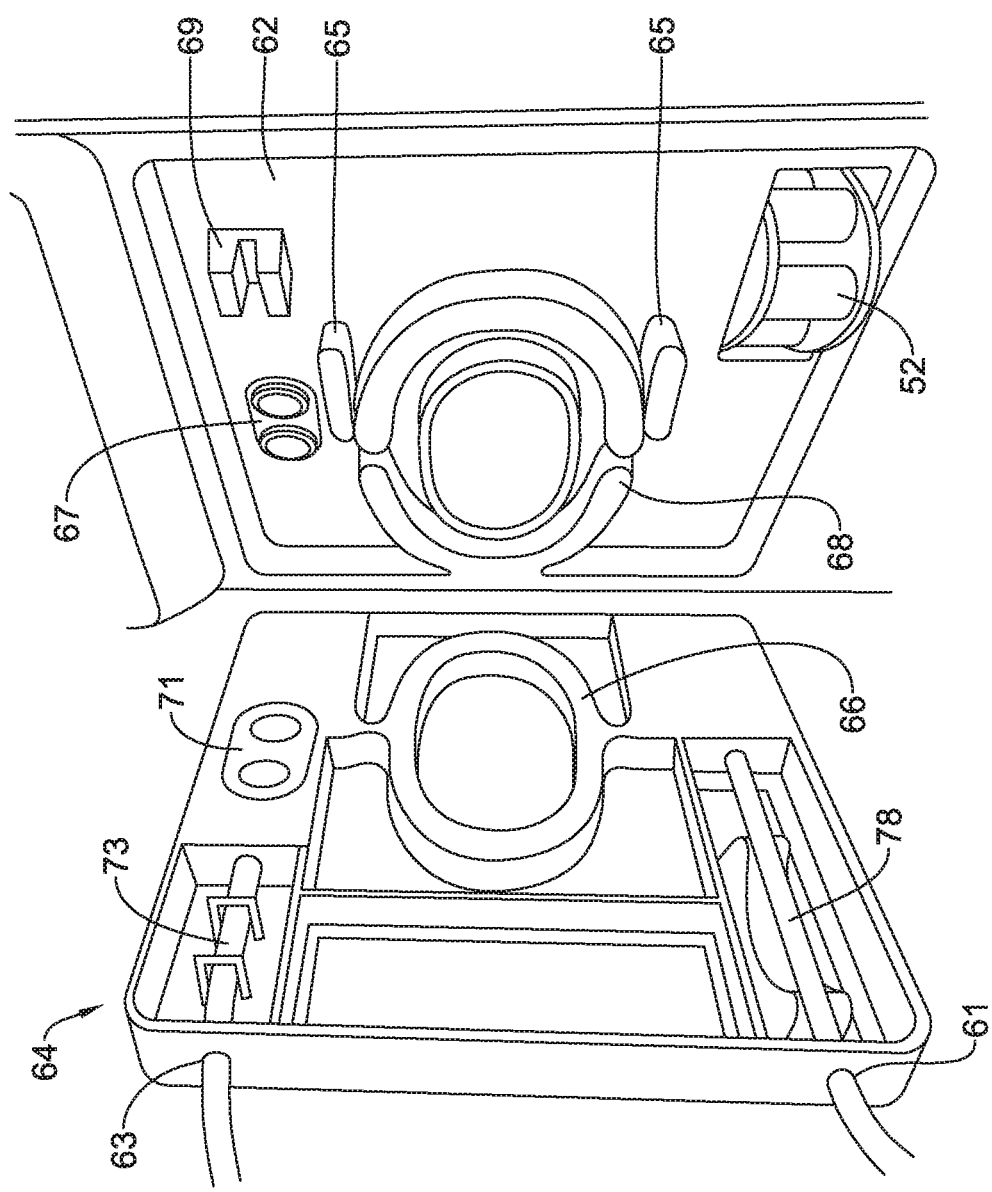
FIG. 5 is a partial perspective view of the heater assembly and cassette of the system of FIG. 1 according to an illustrative embodiment.

In an illustrative embodiment, the fluid management system 10 may optionally include a fluid warming system 60 for heating fluid to be delivered to the patient, as shown in FIG. 5. The fluid warming system 60 includes a heater 62 and a heater cassette 64. The cassette 64 may be configured to be a single use cassette 64 while the heater 62 may be reused for multiple procedures. For example, the cassette 64 may isolate fluid flow such that the heater 62 may be reused with minimal maintenance. The cassette 64 may be formed of, for example, polycarbonate or any high heat rated biocompatible plastic and is formed as a single piece or a plurality of pieces permanently bonded to one another. An illustrative cassette 64 may include a fluid inlet port 61 and a fluid outlet port 63 located at a lateral side of the cassette 64. The fluid inlet and outlet ports 61, 63 may each be configured to couple to a tube 78 of the fluid management system 10. For example, the fluid inlet port 61 may couple the fluid source 34 and the fluid warming system 60 (via the pump 52) while the outlet port 63 may couple the fluid warming system 60 with the medical device 20 each via the fluid tubing 78.

In an illustrative embodiment, the cassette 64 includes an internal flow path along a channel through which fluid may flow from the fluid inlet 61 to the fluid outlet 63. The cassette 64 may include one fluid path or multiple fluid paths. In some cases, the channel may pass through a susceptor 66 which may allow the fluid to be heated via induction heating. When the cassette 64 is coupled with the heater 62, the susceptor 66 may be configured to be positioned within an induction coil 68. Other heater configurations and methods may also be used, as desired. For example, the heater 62 may include one or more heat sources such as, for example a platen system or an in line coil in the fluid supply line using electrical energy. Heating may be specifically designed and tailored to the flow rates required in the specific application of the fluid management system 10. Some illustrative heater systems 60 are described in described in commonly assigned U.S. Patent Publication Number 2018/0361055, titled AUTOMATED FLUID MANAGEMENT SYSTEM, the disclosure of which is hereby incorporated by reference.

While not explicitly shown, the fluid warming system 60 may include a heater user interface separate from the touch screen interface 42. The heater user interface may simply be a display screen providing a digital display of the internal temperature of the heater. In another embodiment, the user interface may also include temperature adjustment buttons to increase or decrease the temperature of the heater 62. In this embodiment, the heater display screen) may indicate the current temperature of the heater as well as the target temperature to be reached. It is noted that all information output from the fluid warming system 60 may be transmitted directly to the display screen 44 such that no heater user interface is necessary.

The fluid warming system 60 may include one or more sensors configured to monitor the fluid. For example, temperature sensors 65 may be mounted in the fluid warming system 60 such that they detect the temperature of the fluid flowing through the cassette 64. The temperature sensors 65 may be located at or near the fluid inlet port 61 and the fluid outlet port 63. In an illustrative embodiment, the temperature sensors 65 may be mounted so that they detect the temperature of fluid flowing through the cassette 64 prior to the fluid entering the susceptor 66 and after fluid exits the susceptor 66. In some embodiments, additional sensors may be located at a medial portion of the susceptor 66 so that they detect the progression of the temperature increase of the fluid in the cassette 64. The temperature sensors 65 may remotely send any information to the display screen 44 or they may send information to heater user interface display screen, if so provided. In another embodiment, the temperature sensors 65 may be hardwired with the heater user interface (if provided) which is then able to remotely transmit desired information to the system display screen 44. Alternatively, or additionally, the temperature sensors 65 may be hardwired with the main processing device 48.

The heater assembly 62 may further include a pressure sensor 67 and a bubble sensor 69. The cassette 64 may include a corresponding pressure sensor interface 71 and bubble sensor interface 73 that allow the sensors 67, 69 to monitor the fluid flowing through the cassette 64 when the cassette is coupled with the fluid warming system 60. The pressure sensor 67 and/or bubble sensor 69 may remotely send any information to the display screen 44 or they may send information to heater user interface display screen, if so provided. In another embodiment, the pressure sensor 67 and/or bubble sensor 69 may be hardwired with the heater user interface (if provided) which is then able to remotely transmit desired information to the system display screen 44. Alternatively, or additionally, the pressure sensor 67 and/or bubble sensor 69 may be hardwired with the main processing device 48.

Figure 6:
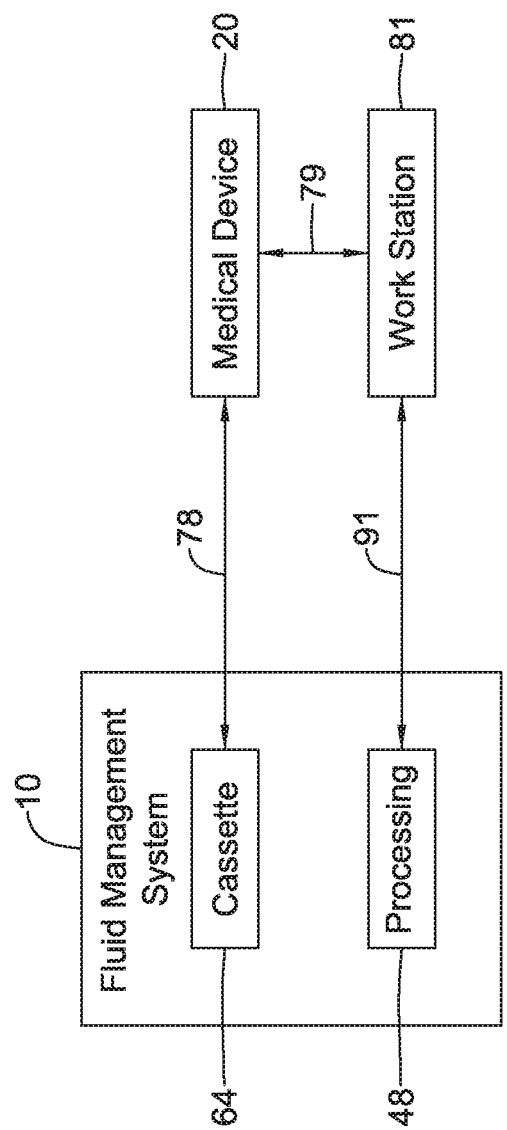
FIG. 6 is a schematic block diagram of the illustrative fluid management system and medical device of FIG. 1.

FIG. 6 is a schematic block diagram illustrating the fluid management system 10 and the medical device 20. As described herein, there may be two primary interfaces between the fluid management system 10 and the medical device 20 including one or more mechanical connections (e.g., fluid tubes 78) fluidly coupling the medical device 20 to the cassette 64 and one or more electrical or communications connections 91 (e.g., an Ethernet cord) coupling the workstation 81 of the medical device with the main processing device 48 of the fluid management system 10. The workstation 81 of medical device 20 may transmit intrarenal pressure measurements (e.g., obtained with the medical device 20) with the main processing device 48 of the fluid management system 10. The main processing device 48 of the fluid management system 10 may then use this pressure data to adjust fluid flow rates when a user specified or predetermined pressure limit is reached.

However, during a typical stone procedure, for example, the fluid management system 10 may be connected to multiple endoscopes, or other medical devices. Also, in a procedure where both the medical device 20 with the pressure sensor 74 and the fluid management system 10 are used, it is may be that the main procession device 48 and the workstation may be connected during the staging of the OR, and main remain connected throughout the procedure. This might mean if a medical device 20 is connected to its workstation 81, the workstation 81 will transmit pressure data to the main processing device 48 of the fluid management system 10 whether or not the medical device 20 is in use. Thus, the main processing device 48 of the fluid management system 10 may be configured to determine when it is safe to use the pressure data from the medical device 20 for regulating intrarenal pressure. In some cases, this may be done by asking the user to select on the touch screen interface 42 the type of scope being used. If the physician selects a device other than the medical device 20, the main processing device 48 of the fluid management system 10 may ignore the pressure data being sent from the medical device 20.

However, there can be cases where the physician incorrectly selects the medical device 20 when the physician is not actually using it or the physician may forget to tell the fluid management system 10 that the medical device 20 is no longer in use and a different scope or medical device is now in use. If the fluid management system 10 is unable to detect that a new scope or medical device is being used, the fluid management system 10 may incorrectly use the pressure data sent from the medical device 20 which is not in use (and therefore the pressure data is inaccurate relative to the intrarenal pressure). As a result, this may essentially bypass the fluid management system 10 pressure limit control and allow the fluid management system 10 to drive or deliver potentially hazardous pressures. To prevent such hazards from occurring, it may be necessary for the fluid management system 10 system to determine when it safe to use the pressure data transmitted from the medical device 20 via the workstation 81. Thus, it may be desirable to detect is a sensor enabled medical device 20 is connected to the fluid management system 10 when the only connection between the medical device 20 and the fluid management system 10 may be a physical connection using, for example, a standard Luer connector.

When the medical device 20 is in use with the fluid management system 10, the medical device 20 may be exposed to several unique sources of pulsatile pressures that can be measured by the pressure sensor 74 at the tip of the medical device 20. These sources of pulsation can either be unique to the fluid management system 10 or to the patient. If one or more sources of pulsation can be distinguished, the fluid management system 10 can make the determination that the medical device 20 is in use and thus safe to limit pressure based off the pressure measurements from the medical device 20.

One source of pulsatile pressure may be generated within the fluid management system 10. For example, a peristaltic fluid pump 52 may create a unique fingerprint in its pulsatile flow that can be measured with a pressure sensor, such as the pressure sensor 74 on the medical device 20. The pulsatility may be a function of the pump head rollers and the revolutions per minute (RPM) of the pump head. When the medical device 20 is connected to the fluid management system 10, this fingerprint can be measured by the medical device 20 and matched against the signature created by the pump mechanism of the fluid management system 10. When there is a match between the measured pressure pulsatile flow at the pressure sensor 74 of the medical device 20 and the known signature of the pump 52 of the fluid management system 10, the fluid management system 10 can confirm the medical device 20 is in use and connected to the fluid management system 10.

Figure 7A:
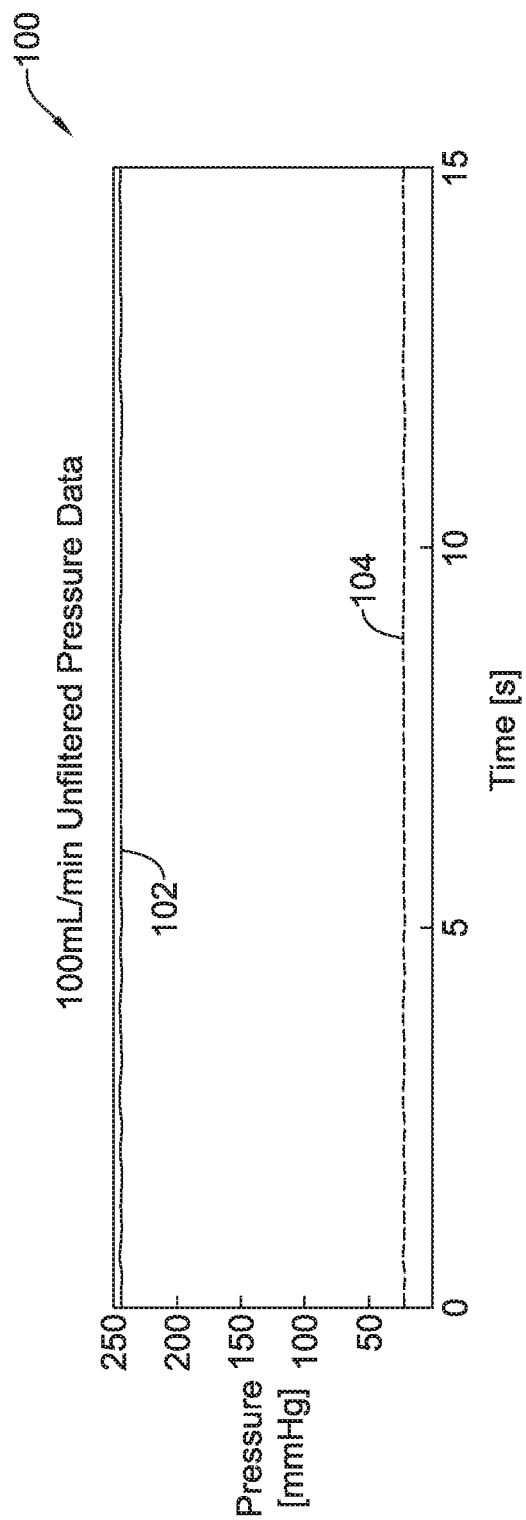
FIGS. 7A-7C are a set of illustrative graphs of pressure data from the fluid management system and the medical devices.
Figure 7B:
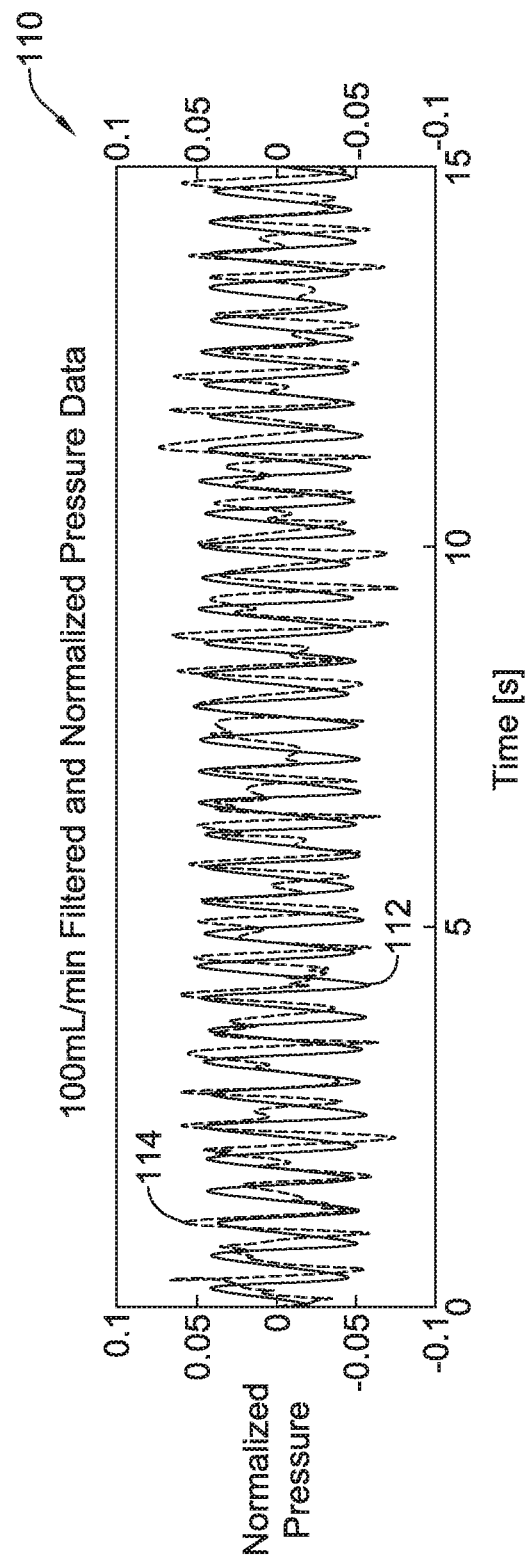
Figure 7C:
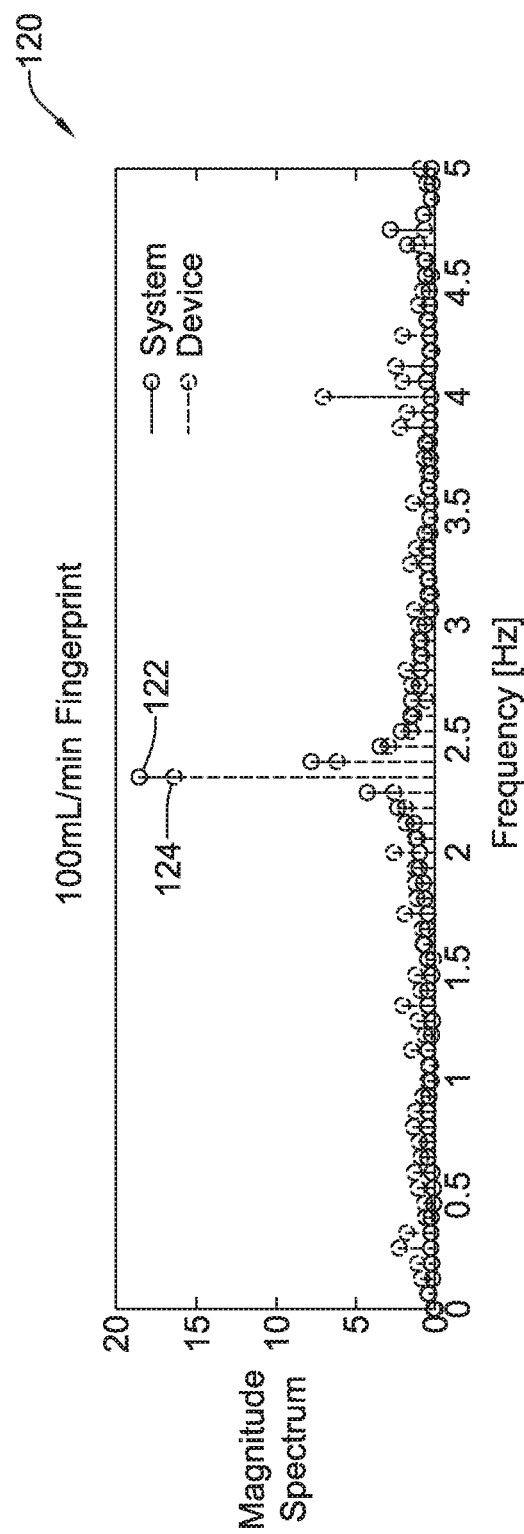

FIG. 7A is an illustrative graph 100 of unfiltered raw pressure data 102 from the fluid management system 10 and unfiltered raw pressure data 104 from the medical device 20. In some cases, the raw pressure data 102 from the fluid managements system 10 may be received from the pressure sensor 67 in the heater system 60. In other embodiments, the pressure data 102 may be retrieved from a database of expected pressures according to fluid flow rate. In the illustrative embodiment, the data 102, 104 is collected at a medium flow rate of about 100 milliliters per minute (mL/min). However, it should be understood that the data processing steps described herein may be used for flow rates less than 100 mL/min and greater than 100 mL/min. In order to compare the pressure data 102 from the fluid management system 10 and pressure data 104 from the medical device, the data 102, 104 may be filtered using math averaging. To begin, the DC component of each measured waveform 102, 104 may be filtered. In some cases, the data 102, 104 may be filtered with a low pass filter with a filter cutoff frequency. The filter cutoff frequency may be set based off of the pump flow rate. The data 102, 104 may then be normalized. FIG. 7B is a graph 110 of the filtered and normalized pressure data 112 from the fluid management system 10 and the filtered and normalized pressure data 114 from the medical device 20. Next, a fast Fourier transform (FFT) algorithm may be performed on the filtered and normalized data 112, 114 to extract the dominant tone created by the pump 52. The FFT algorithm may convert the filtered and normalized data 112, 114 from the time domain to the frequency domain. FIG. 7C is a graph 120 of the filtered and normalized pressure data of the fluid management system 10 and the filtered and normalized pressure data of the medical device 20 in the frequency domain. When the filtered and normalized pressure data 112, 114 is converted to the frequency domain, the dominant tone 122 (e.g., the frequency having the greatest magnitude) of the fluid management system 10 and the dominant tone 124 of medical device 20 can be identified. As can be seen in FIG. 7C, in the illustrative embodiment, the dominant tone 122 of the fluid management system 10 and the dominant tone 124 of the medical device 20 are similar or the same at about 2.3 Hertz (Hz). In the illustrated example, the fluid management system 10 may determine that the dominant tones 12, 124 match. The dominant tones 122, 124 may be considered to match if they are equal, approximately equal, or within a predetermined range of one another. When the dominant tone 122 of the fluid management system 10 and the dominant tone 124 of the medical device 20 match, the fluid management system 10 can determine that the medical device 20 is in use and connected to the fluid management system 10 and the data from the medical device 20 can be used to control fluid management system 10.

It is contemplated that the data processing may occur at the main processing device 48, the workstation 81, or combinations thereof. In some embodiments, all of the raw pressure data 102, 104 may be processed and analyzed at a single processing device. In other embodiments, the raw pressure data 102, 104 may be processed at separate processing devices. For example, in some cases, the main processing device 48 may process (e.g., filter, normalized, and/or FFT) the raw pressure data 102 obtained from the fluid management system 10 while the workstation 81 may process (e.g., filter, normalize, and/or FFT) the raw pressure data 104 obtained from the medical device 20. In some cases, the processed medical device data may be transferred from the workstation 81 to the main processing device 48 for comparison. In other embodiments, the processed fluid management system data may be transferred from the main processing device 48 to the workstation 81 for analysis.

Figure 8A:
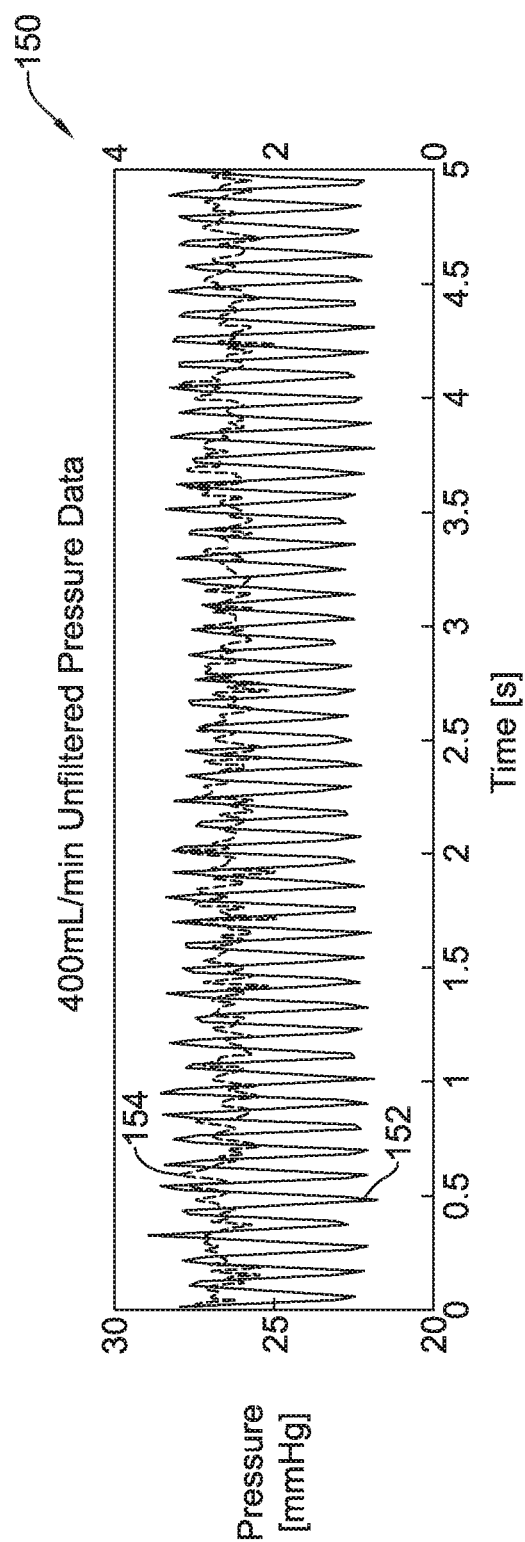
FIGS. 8A-8C are another set of illustrative graphs of pressure data from the fluid management system and the medical devices.
Figure 8B:
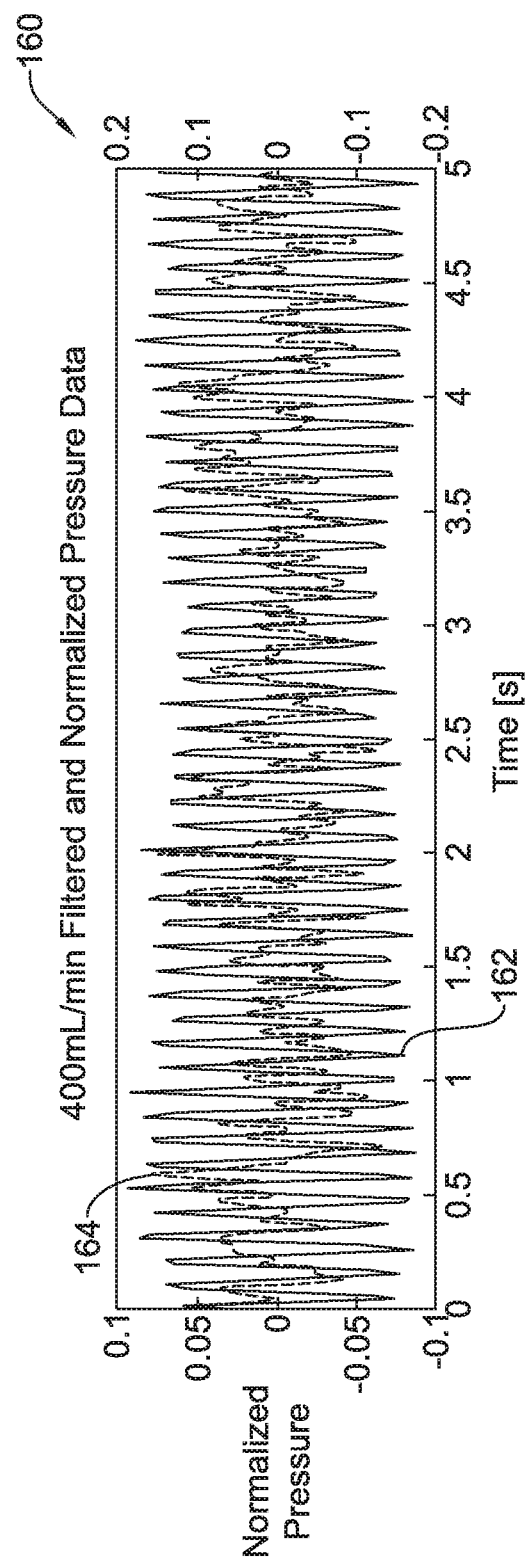
Figure 8C:
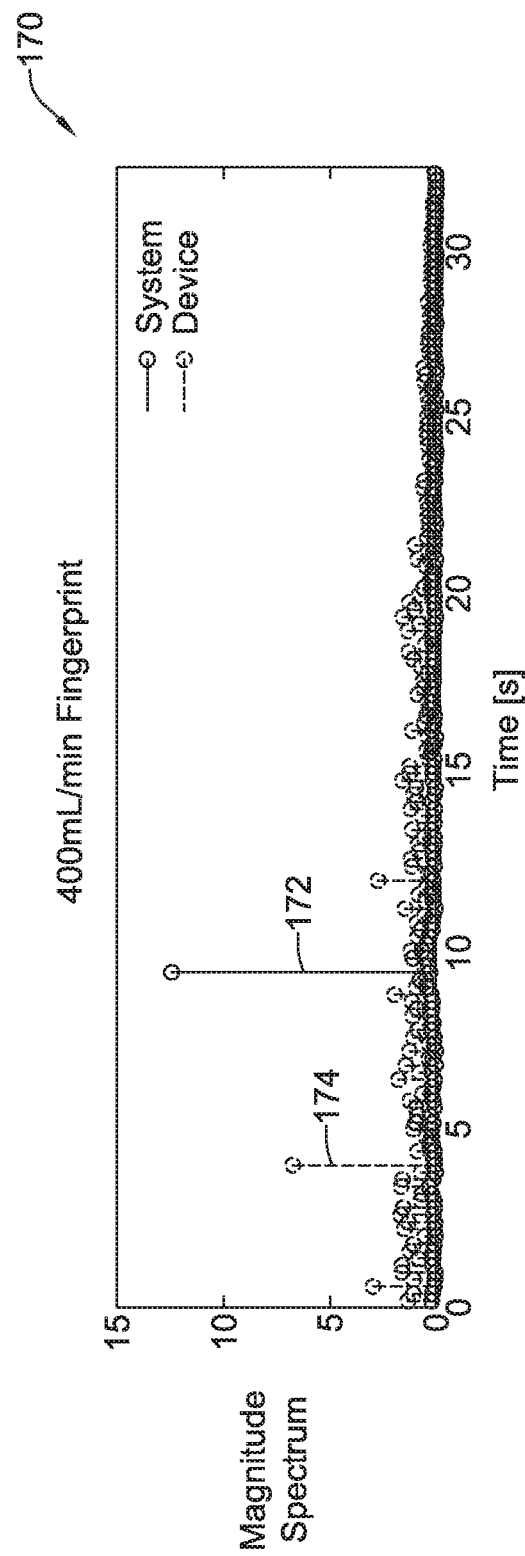

FIGS. 8A-8C illustrate the processing of another pressure data set. FIG. 8A is an illustrative graph 150 of unfiltered raw pressure data 152 from the fluid management system 10 and unfiltered raw pressure data 154 from the medical device 20. In the illustrative embodiment, the data 152, 154 is collected at a higher flow rate of about 400 milliliters per minute (mL/min). However, it should be understood that the data processing steps described herein may be used for flow rates less than 400 mL/min and greater than 400 mL/min. In order to compare the pressure data 152 from the fluid management system 10 and pressure data 154 from the medical device, the data 152, 154 may be filtered using math averaging. To begin, the DC component of each measured waveform 152, 154 may be filtered. In some cases, the data 152, 154 may be filtered with a low pass filter with a filter cutoff frequency. The filter cutoff frequency may be set based off of the pump flow rate. The data 152, 154 may then be normalized. FIG. 8B is a graph 160 of the filtered and normalized pressure data 162 from the fluid management system 10 and the filtered and normalized pressure data 164 from the medical device 20. Next, a fast Fourier transform (FFT) algorithm may be performed on the filtered and normalized data 162, 164 to extract the dominant tone created by the pump 52. The FFT algorithm may convert the filtered and normalized data 162, 164 from the time domain to the frequency domain. FIG. 8C is a graph 170 of the filtered and normalized pressure data of the fluid management system 10 and the filtered and normalized pressure data of the medical device 20 in the frequency domain. When the filtered and normalized pressure data 162, 164 is converted to the frequency domain, the dominant tone 172 (e.g., the frequency having the greatest magnitude) of the fluid management system 10 and the dominant tone 174 of medical device 20 can be identified. As can be seen in FIG. 8C, in the illustrative embodiment, the dominant tone 172 of the fluid management system 10 and the dominant tone 174 of the medical device 20 are not similar or the same. For example, the dominant tone 172 of the fluid management system 10 is about 9.5 Hz while the dominant tone 174 of the medical device is about 4 Hz. In this example, the fluid management system 10 may determine that the dominant tones 172, 174 do not match and the thus the data from the medical device 20 should not be used to control the fluid management system 10.

Another source of pulsatile pressure may be the patient's heartbeat. For example, pulsatile waves, which are synchronous with the heartbeat, may be transmitted to within the renal pelvis. These pulsatile waves may create a unique pressure signature related to the cardiac rhythm that can be detected by the medical device 20. The fluid management system 10 may be configured to compare a characteristic extracted from the pressure signature of the heartbeat with a characteristic extracted from data received from the pressure sensor 74 on the medical device 20. The characteristic may be a frequency, amplitude, dominant tone, etc. In one example, the fluid management system 10 may compare heartbeat data that has been filtered, normalized and converted to the frequency domain to pressure data from the medical device 20 that has also been filtered, normalized and converted to the frequency domain in a manner similar to that described with respect to FIGS. 7A-7C and FIGS. 8A-8C. It is contemplated that the heartbeat data may be obtained from a medical device other than the fluid management system 10 or the medical device 20. If the cardiac rhythm is detected in the medical device 20 pressure measurements, the fluid management system 10 can make the determination that medical device 20 is in use and thus the fluid management system 10 can use data obtained from the medical device 20 to control the fluid management system 10. If the cardiac rhythm cannot be detected in the medical device 20 pressure measurements, the fluid management system 10 can make the determination that medical device 20 is not in use and the fluid management system 10 should not use pressure measurements from the medical device 20.

Another source of pulsatile pressure may be the ureteral renal pelvic activity of the patient. For example, the contraction and relaxation of the patient's ureter or renal pelvis may create a unique and measurable pressure wave. The periodic from these contractions may be detected with the pressure sensor 74 in the medical device 20. The fluid management system 10 may be configured to compare a characteristic extracted from the pressure signature of the ureteral renal pelvic activity with a characteristic extracted from data received from the pressure sensor 74 on the medical device 20. The characteristic may be a frequency, amplitude, dominant tone, etc. In some cases, the contractions may be detected with a sensor other than the medical device 20 or the fluid management system 10 for comparison to pressure data from the medical device 20. In other embodiments, the fluid management system 10 may be configured to compare an expected or preprogrammed contraction pattern with the pressure data from the medical device 20. It is contemplated that the contraction data (if obtained during the medical procedure) may be filtered, normalized and converted to the frequency domain prior to comparison with the pressure data from the medical device which has also been filtered, normalized and converted to the frequency domain in a manner similar to that described with respect to FIGS. 7A-7C and FIGS. 8A-8C. If the ureteral renal pelvic activity is detected in the medical device 20 pressure measurements, the fluid management system 10 can make the determination that medical device 20 is in use and thus the fluid management system 10 can use data obtained from the medical device 20 to control the fluid management system 10. If the ureteral renal pelvic activity cannot be detected in the medical device 20 pressure measurements, the fluid management system 10 can make the determination that medical device 20 is not in use and the fluid management system 10 should not use pressure measurements from the medical device 20.

Yet another source of pulsatile pressure may be the patient's respiration. For example, the normal respiratory rhythm of the patient may create slow, time varying changes in intrarenal pressure. These slow changes in pressure may be measured by the pressure sensor 74 on the medical device 20 (when the medical device 20 is in use) and matched to the patient's respiratory rhythm. The fluid management system 10 may be configured to compare a characteristic extracted from the pressure signature of the respiratory rhythm with a characteristic extracted from data received from the pressure sensor 74 on the medical device 20. The characteristic may be a frequency, amplitude, dominant tone, etc. In an example, the fluid management system 10 may compare respiration data that has been filtered, normalized and converted to the frequency domain to pressure data from the medical device 20 that has also been filtered, normalized and converted to the frequency domain in a manner similar to that described with respect to FIGS. 7A-7C and FIGS. 8A-8C. It is contemplated that the respiration data may be obtained from a medical device other than the fluid management system 10 or the medical device 20. If the respiration rhythm is detected in the medical device 20 pressure measurements, the fluid management system 10 can make the determination that medical device 20 is in use and thus the fluid management system 10 can use data obtained from the medical device 20 to control the fluid management system 10. If the respiration rhythm cannot be detected in the medical device 20 pressure measurements, the fluid management system 10 can make the determination that medical device 20 is not in use and the fluid management system 10 should not use pressure measurements from the medical device 20.

Figure 9:
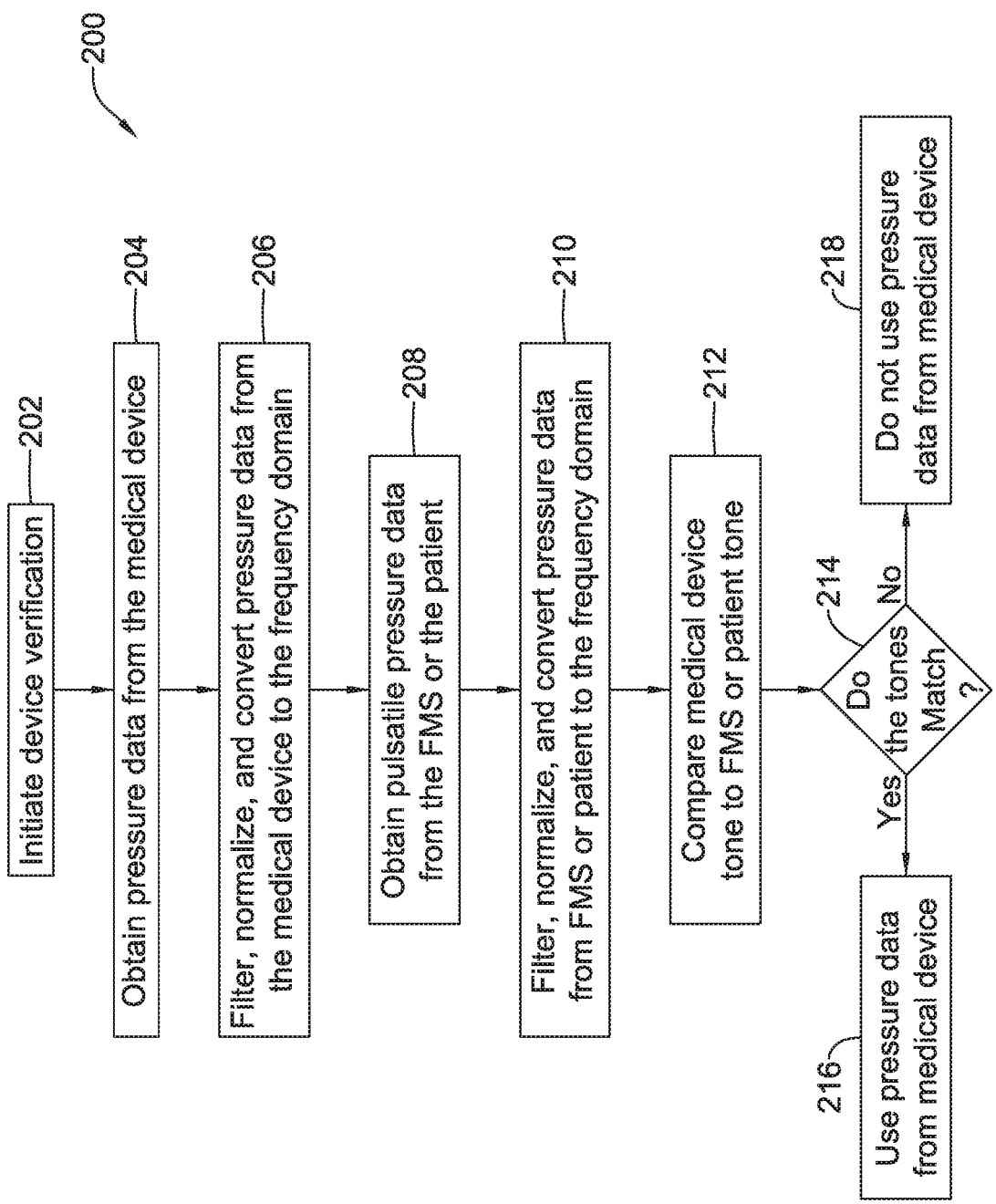
FIGS. 9-12 are illustrative flow charts of methods for determining if data from the medical device can be used to control the fluid management system.

FIG. 9 is an illustrative flow chart 200 of a method for using pulsatile pressures to determine if the medical device 20 is in use within the body of the patient. To begin, the main processing device 48 of the fluid management system 10 may initiate a device verification process, as shown at block 202. It is contemplated that the main processing device 48 may be configured to perform the check at predetermined intervals during the procedure (e.g., every minute, every five minutes, etc.). In other embodiments, the main processing device 48 may be configured to perform the device verification each time the fluid processing system attempts to use pressure data from the medical device 20 to control fluid flow from the fluid management system. Additionally, or alternatively, the device verification may be manually initiated. For example, the physician may initiate device verification using the touch screen interface 42. The fluid management system 10 may then obtain pressure data from the medical device 20, as shown at block 204. In some cases, the main processing device 48 of the fluid management system 10 may poll the workstation 81 of the medical device 20 for raw data over a predetermined time period, although this is not required. In some cases, the main processing device 48 may command the workstation 81 to obtain the pressure data from the medical device 20. The pressure data from the medical device 20 may then be filtered, normalized, and converted to the frequency domain, as shown at block 206. It is contemplated that the pressure data from the medical device 20 may be processed at the main procession device 48 of the fluid management system 10 or at the workstation 81 of the medical device 20, as desired.

The fluid management system 10 may also obtain pulsatile pressure data from the fluid management system 10 and/or the patient, as shown at block 208. Sources of pulsatile pressure data may include, but are not limited to, the pressure pulses generated by a peristaltic pump 52, the patient's heartbeat, the patient's ureteral renal pelvic activity, the patient's respiratory rhythm, etc. It is contemplated that the fluid management system 10 may be configured to obtain the pulsatile pressure data over the same predetermined time period as (e.g., substantially simultaneously with) the pressure data from the medical device 20. However, in some instances, the fluid management system 10 may not obtain new data related to the pulsatile pressure data, but rather reference a predetermined baseline or expected data. The pressure data from the fluid management system 10 and/or the patient may then be filtered, normalized, and converted to the frequency domain, as shown at block 210. It is contemplated that the pressure data from the fluid management system 10 and/or the patient may be processed at the main processing device 48 of the fluid management system 10 or at the workstation 81 of the medical device 20, as desired.

The main processing device 48 of the fluid management system 10 or the workstation 81 may then compare the frequency domain data of the medical device 20 with the frequency domain data of the pulsatile pressure source, as shown at block 212. The main processing device 48 of the fluid management system 10 or the workstation 81 may then determine if the frequency domain data of the medical device 20 and the frequency domain data of the pulsatile pressure source match, as shown at block 214. If the frequency domain data of the medical device 20 and the frequency domain data of the pulsatile pressure source match, the fluid management system 10 determines the pressure data from the medical device 20 can be used to control the fluid flow from the fluid management system 10, as shown at block 216. If the frequency domain data of the medical device 20 and the frequency domain data of the pulsatile pressure source do not match, the fluid management system 10 determines the pressure data from the medical device 20 cannot or should not be used to control the fluid flow from the fluid management system 10, as shown at block 218.

Figure 10:
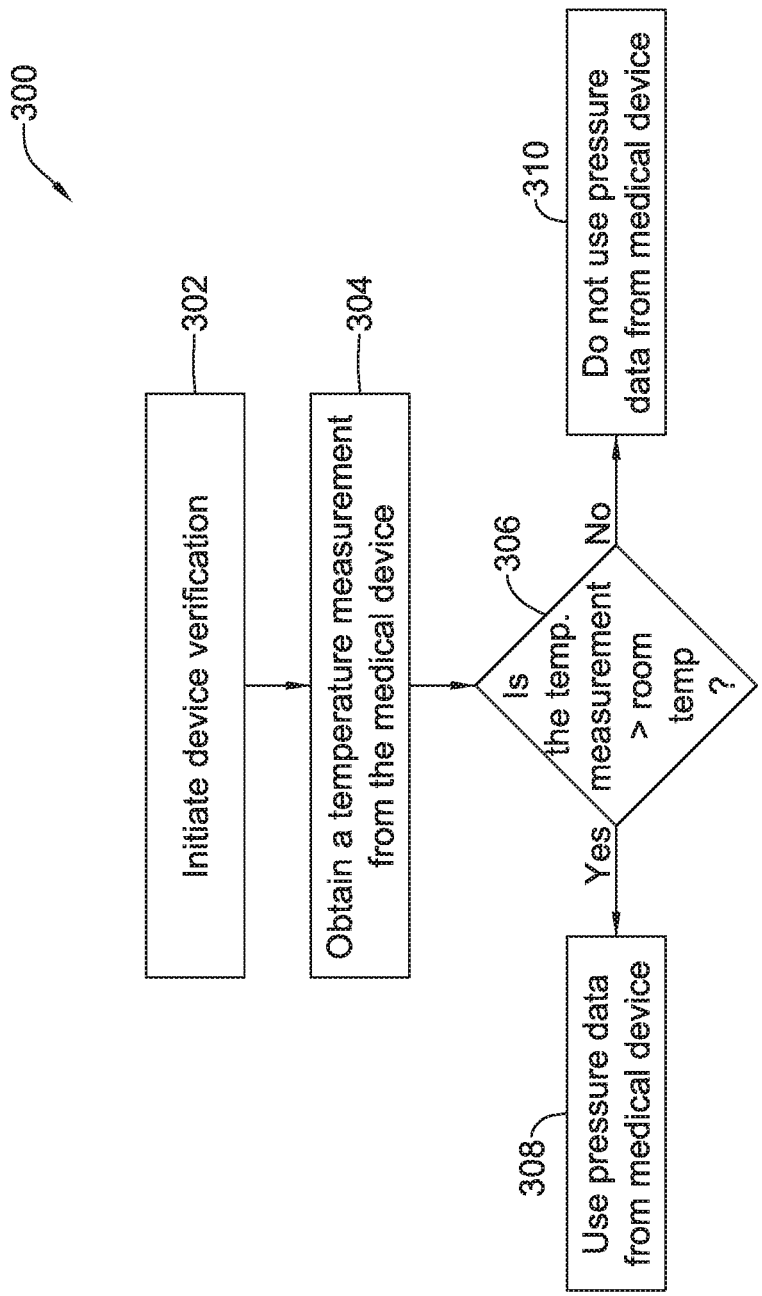

Alternatively, or additionally, the data obtained from the temperature sensor 72 of the medical device 20 may be used to determine if the data from the pressure sensor 74 can be used to help control the fluid management system 10. FIG. 10 is an illustrative flow chart 300 of a method for using temperature measurements from the medical device 20 to determine if the medical device 20 is in use within the body of the patient. To begin, the main processing device 48 of the fluid management system 10 may initiate a device verification process, as shown at block 302. It is contemplated that the main processing device 48 may be configured to perform the check at predetermined intervals during the procedure (e.g., every minute, every five minutes, etc.). In other embodiments, the main processing device 48 may be configured to perform the device verification each time the fluid processing system attempts to use pressure data from the medical device 20 to control fluid flow from the fluid management system 10. Additionally, or alternatively, the device verification (block 302) may be manually initiated. For example, the physician may initiate device verification using the touch screen interface 42. The fluid management system 10 may then obtain temperature data from the medical device 20, as shown at block 304. In some cases, the main processing device 48 of the fluid management system 10 may poll the workstation 81 of the medical device 20 for raw data over a predetermined time period, although this is not required. In some cases, the main processing device 48 may command the workstation 81 to obtain the temperature data from the medical device 20.

The main processing device 48 of the fluid management system 10 or the workstation 81 may then determine if the temperature measurement from the medical device 20 is greater than room temperature (e.g., greater than about 20° C.-23° C.), as shown at block 306. In some cases, the main processing device 48 of the fluid management system 10 or the workstation 81 may then determine if the temperature measurement from the medical device 20 is around body temperature (e.g., about 37° C.). If the temperature measurement obtained from the temperature sensor 72 on the medical device 20 is greater than 20° C.-23° C. (e.g., room temperature) or about 37° C. (e.g., body temperature), the fluid management system 10 determines the pressure data from the medical device 20 can be used to control the fluid flow from the fluid management system 10, as shown at block 308. If the temperature measurement obtained from the temperature sensor 72 on the medical device 20 is about 20° C.-23° C. (e.g., room temperature) or less 37° C. (e.g., body temperature), the fluid management system 10 determines the pressure data from the medical device 20 cannot or should not be used to control the fluid flow from the fluid management system 10, as shown at block 310. In some cases, the fluid management system 10 may be configured to determine the medical device 20 is in use any time the temperature measurement obtained at the temperature sensor 72 is greater than room temperature (e.g., greater than about 20° C.-23° C.). The fluid management system 10 may compare the temperature measurement obtained at the temperature sensor 72 to an ambient temperature measurement of the room (an accurately measured room temperature). In other cases, the fluid management system 10 may be configured such that any temperature measurement greater than 25° C., greater than 28° C., or greater than 30° C. obtained at the temperature sensor is above room temperature and thus the data from the medical device 20 is safe to use.

It is contemplated that the fluid management system 10 may be programmed with a first temperature range that may be considered about room temperature (e.g., 20° C.+/−5° C. or 23° C.+/−3° C.) or an accurate room temperature measurement may be inputted into the fluid management system 10 from a ambient temperature sensor provided with or otherwise communicating with the fluid management system, and a second temperature range that may be considered about body temperature (e.g., 37° C.+/−1° C. or 37° C.+/−2° C.). These are just examples. Other temperature ranges may be used as desired or appropriate for the environmental conditions. In some cases, a body temperature range may be selected that accounts for procedures in which the fluid management system 10 delivers fluid at temperatures greater than body temperature (e.g., for example when a laser is in use). In other cases, a body temperature range may be selected that accounts for procedures in which the fluid management system 10 delivers fluid at temperatures less than body temperature.

Figure 11:
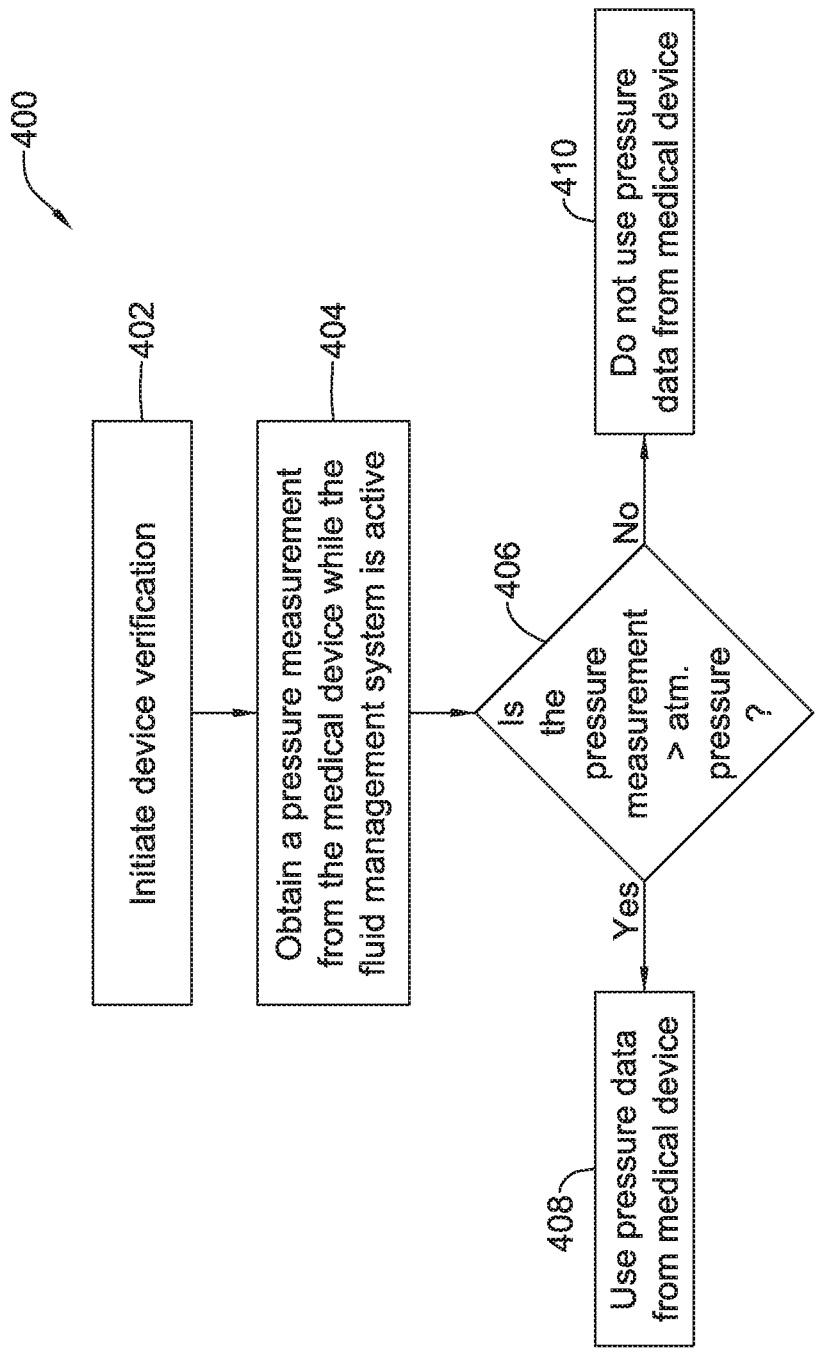

Alternatively, or additionally, the data obtained from the pressure sensor 74 of the medical device 20 may be compared to atmospheric pressure to determine if the data from the pressure sensor 74 of the medical device can be used to help control the fluid management system 10. FIG. 11 is an illustrative flow chart 400 of another method for using pressure measurements from the medical device 20 to determine if the medical device 20 is in use within the body of the patient. To begin, the main processing device 48 of the fluid management system 10 may initiate a device verification process, as shown at block 402. It is contemplated that the main processing device 48 may be configured to perform the check at predetermined intervals during the procedure (e.g., every minute, every five minutes, etc.). In other embodiments, the main processing device 48 may be configured to perform the device verification each time the fluid processing system attempts to use pressure data from the medical device 20 to control fluid flow from the fluid management system 10. Additionally, or alternatively, the device verification (block 402) may be manually initiated. For example, the physician may initiate device verification using the touch screen interface 42. The fluid management system 10 may then obtain pressure data from the medical device 20 while the fluid management system 10 is actively delivering fluid, as shown at block 404. In some cases, the main processing device 48 of the fluid management system 10 may poll the workstation 81 of the medical device 20 for raw data over a predetermined time period, although this is not required. In some cases, the main processing device 48 may command the workstation 81 to obtain the pressure data from the medical device 20.

It is contemplated that if the medical device 20 is in the body while the fluid management system 10 is delivering fluid, the pressure measured at the pressure sensor 74 of the medical device 20 will be greater than atmospheric pressure. The main processing device 48 of the fluid management system 10 or the workstation 81 may then determine if the pressure measurement from the medical device 20 is greater than atmospheric pressure, as shown at block 406. If the pressure measurement obtained from the pressure sensor 74 on the medical device 20 is above atmospheric pressure, the fluid management system 10 determines the pressure data from the medical device 20 can be used to control the fluid flow from the fluid management system 10, as shown at block 408. If the pressure measurement obtained from the pressure sensor 74 on the medical device 20 is at or about atmospheric pressure, the fluid management system 10 determines the pressure data from the medical device 20 cannot or should not be used to control the fluid flow from the fluid management system 10, as shown at block 410. It is contemplated that an average pressure measurement and/or a root mean square (RMS) DC pressure from the pressure sensor 74 may be used to compare against atmospheric pressure.

Figure 12:
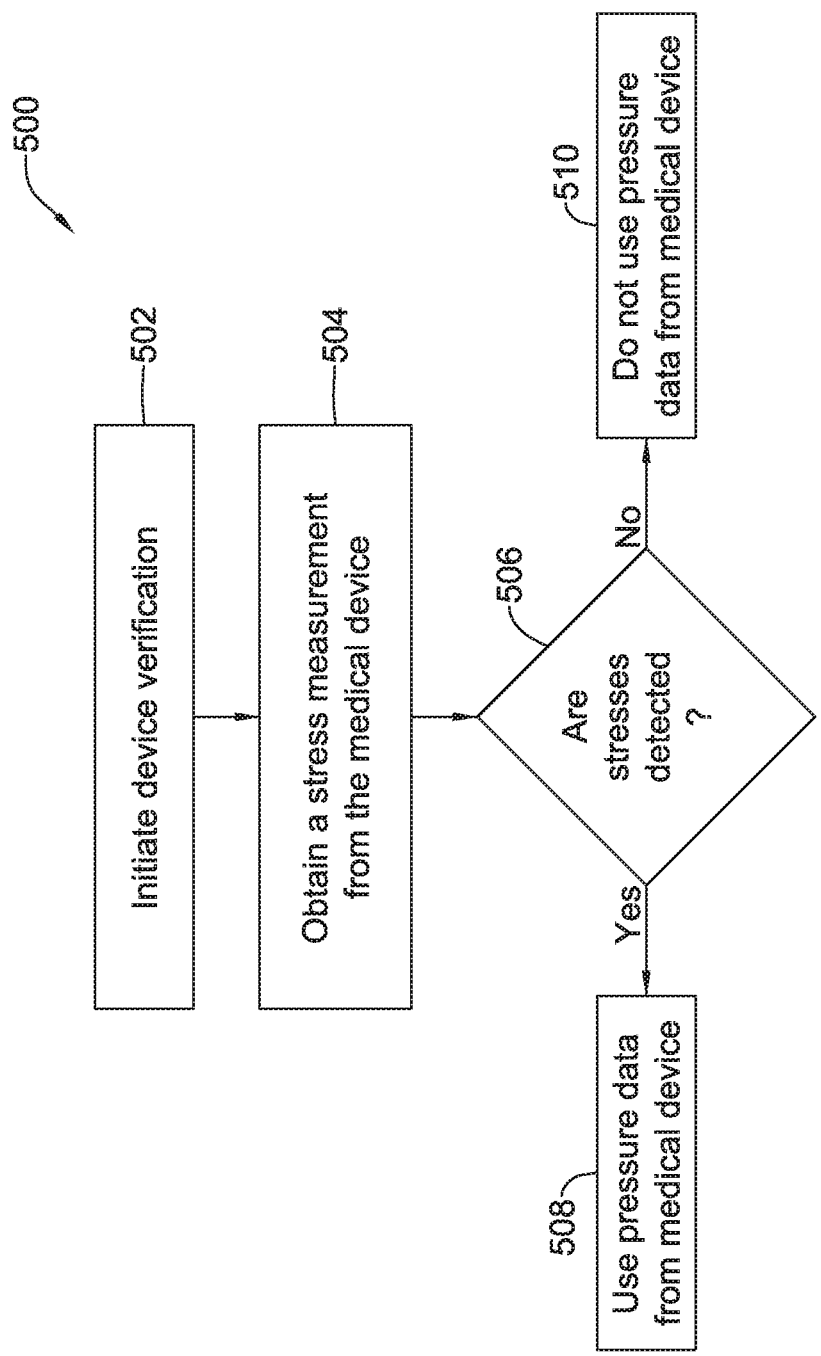

Alternatively, or additionally, data obtained from the Fiber Bragg grating optical fiber 75 at a distal end 80 of the medical device 20 may be used to determine if the data from the pressure sensor 74 of the medical device 20 can be used to help control the fluid management system 10. For example, the Fiber Bragg grating optical fiber 75 may detect stress along the shaft 76 of the medical device 20 that occurs during normal use of the medical device 20. FIG. 12 is an illustrative flow chart 500 of a method for using stress measurements from the medical device 20 to determine if the medical device 20 is in use within the body of the patient. To begin, the main processing device 48 of the fluid management system 10 may initiate a device verification process, as shown at block 502. It is contemplated that the main processing device 48 may be configured to perform the check at predetermined intervals during the procedure (e.g., every minute, every five minutes, etc.). In other embodiments, the main processing device 48 may be configured to perform the device verification each time the fluid processing system attempts to use pressure data from the medical device 20 to control fluid flow from the fluid management system 10. Additionally, or alternatively, the device verification (block 502) may be manually initiated. For example, the physician may initiate device verification using the touch screen interface 42. The fluid management system 10 may then obtain stress data from the Fiber Bragg grating optical fiber 75, or other stress measurement device, at a distal end 80 of the medical device 20, as shown at block 504. In some cases, the main processing device 48 of the fluid management system 10 may poll the workstation 81 of the medical device 20 for raw data over a predetermined time period, although this is not required. In some cases, the main processing device 48 may command the workstation 81 to obtain the stress data from the medical device 20.

It is contemplated that if the medical device 20 is in the body, the Fiber Bragg grating optical fiber 75 may detect stresses in the elongate shaft 76 caused by normal use of the medical device. The main processing device 48 of the fluid management system 10 or the workstation 81 may then determine if the stress measurements from the medical device 20 are detected, as shown at block 506. If stresses are detected, the fluid management system 10 determines the pressure data from the medical device 20 can be used to control the fluid flow from the fluid management system 10, as shown at block 508. If stresses are not detected, the fluid management system 10 determines the pressure data from the medical device 20 cannot or should not be used to control the fluid flow from the fluid management system 10, as shown at block 510. In some cases, the stress measurements may be compared to a predetermined threshold. For example, if the stresses are above a certain level the medical device 20 is in use while if the stresses are at or below the certain level, the medical device 20 is not in use.

Figure 13:
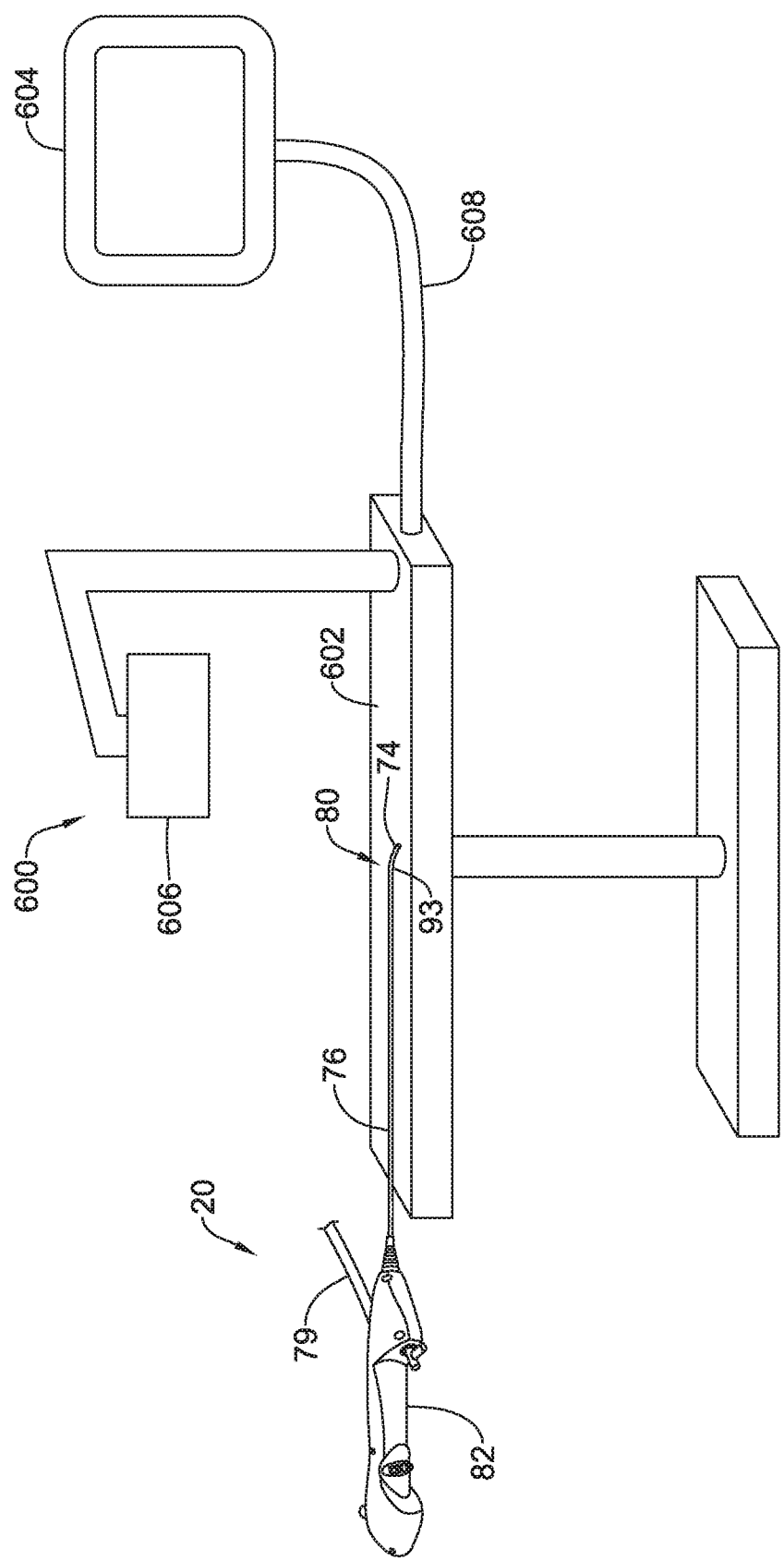
FIG. 13 is a schematic perspective view of an illustrative mapping and navigation system.

Alternatively, or additionally, the location of the distal end 80 of the medical device 20 may be tracked to determine if the medical device 20 is in use. FIG. 13 is schematic view of an illustrative anatomical mapping and navigation system 600. The mapping and navigation system 600 may include an operating table 602 (or other procedural or examination table or chair, etc.). The operating table 602 may be configured to act or function as an electromagnetic generator to generate a magnetic field of a known geometry. Alternatively or additionally, an electromagnetic generator 606 separate from the operating table 602 may be provided. The operating table 602 and/or the electromagnetic generator 606 may be coupled to a control unit 604 which may include among other features, a processor, a memory, a display, and an input means.

A position sensor 93, such as, but not limited to an electromagnetic sensor 93, or other antenna, may be incorporated into the distal end 80 of the elongate shaft 76 of the medical device 20. The position sensor 93 may be configured for use in sensing a location of the position sensor in a magnetic field of a mapping and navigation system 600. The electromagnetic sensor 93 may be coupled to the workstation 81 of the medical device 20. When the electromagnetic sensor 93 is in the magnetic field, the position of the electromagnetic sensor 93 can be mathematically determined relative to the electromagnetic field source (e.g., the operating table 602 and/or the electromagnetic generator 606). The workstation 81 and the control unit 604 may communicate to determine the position of the electromagnetic sensor 93 relative to the patient. When the electromagnetic sensor 93 is positioned within the patient, the fluid management system 10 determines the pressure data from the medical device 20 can be used to control the fluid flow from the fluid management system 10. When the electromagnetic sensor is not positioned within the patient, the fluid management system 10 determines the pressure data from the medical device 20 cannot or should not be used to control the fluid flow from the fluid management system 10

Figure 14:
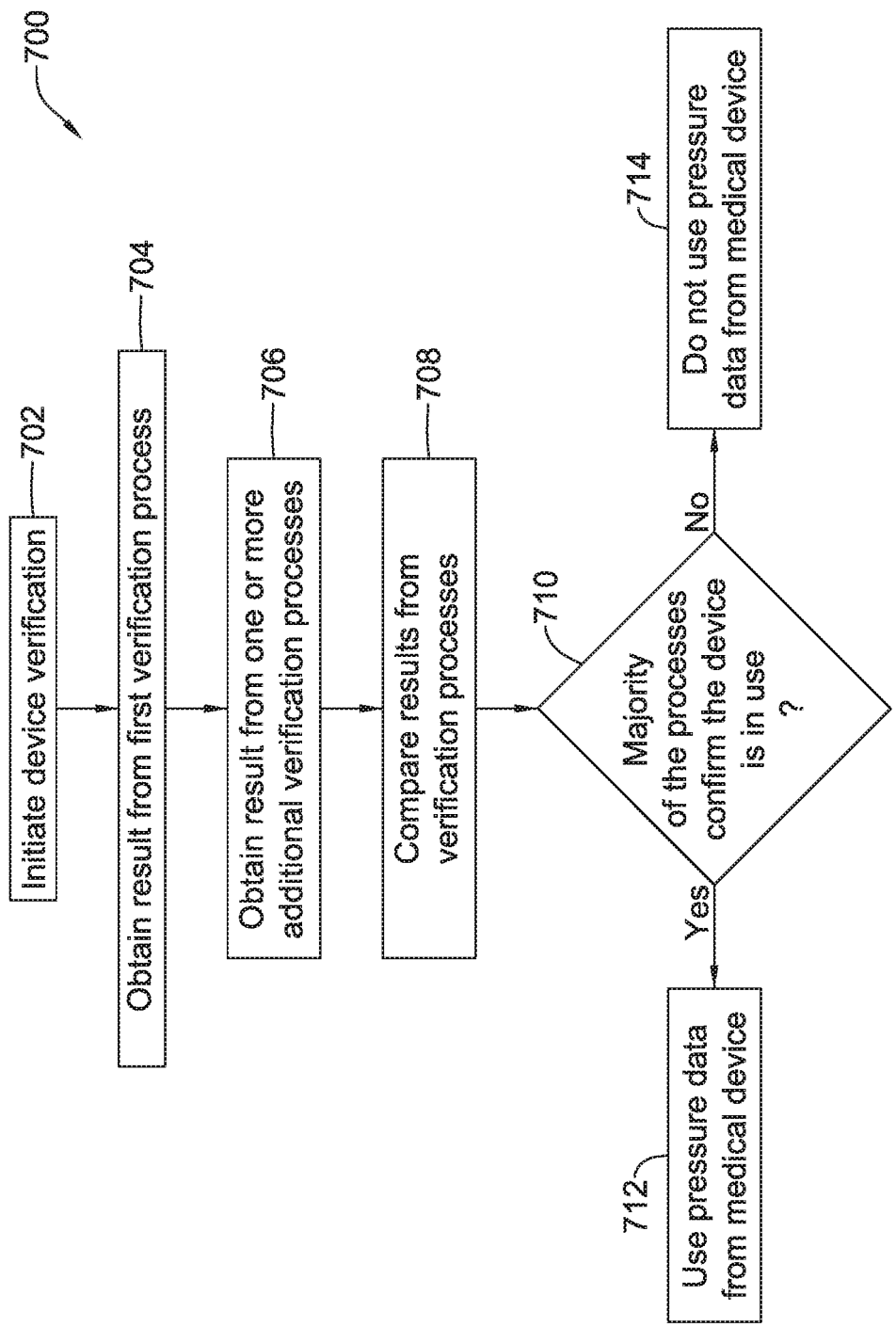
FIG. 14 is another illustrative flow chart of a method for determining if data from the medical device can be used to control the fluid management system.

It may be desirable to reduce the likelihood of falsely determining the medical device 20 is in the body when in actuality, the medical device is not in the body. For example, if the medical device 20 is not in the body but a user touches the temperature sensor 72, the medical device 20 may report to the fluid management system 10 the temperature is near body temperature, thus creating a false detection. It is contemplated that it may be desirable to use more than one sensor or technique to determine if the medical device 20 is in the body. FIG. 14 is an illustrative flow chart of a method 700 for using multiple techniques to determine if the medical device 20 is in the body.

To begin, the main processing device 48 of the fluid management system 10 may initiate a device verification process, as shown at block 702. It is contemplated that the main processing device 48 may be configured to perform the check at predetermined intervals during the procedure (e.g., every minute, every five minutes, etc.). In other embodiments, the main processing device 48 may be configured to perform the device verification each time the fluid processing system attempts to use pressure data from the medical device 20 to control fluid flow from the fluid management system. Additionally, or alternatively, the device verification may be manually initiated. For example, the physician may initiate device verification using the touch screen interface 42. The fluid management system 10 may then obtain a result (the result indicating whether or not the medical device 20 is in the body) from a first verification process or technique, as shown at block 704. The verification process may include, but are not limited to, the use of pulsatile pressures from the pump 52 of the fluid management system, pulsatile pressures from the cardiac cycle, pulsatile pressures from the ureteral renal pelvic activity, pulsatile pressures from the respiratory rhythm, temperature data, atmospheric pressure data, stress detection, location sensing, etc. The fluid management system 10 may also obtain results (the result indicating whether or not the medical device 20 is in the body) from one or more additional verification processes or techniques (different from the first verification process), as shown at block 706. It is contemplated that the results from the two or more verification processes may be obtained substantially simultaneously (e.g., in parallel) or sequentially (e.g., one after the other), as desired. The fluid management system 10 may use any number of verification processes and in any combination, as desired.

The main processing device 48 of the fluid management system 10 may compare the results to determine the number of verification processes that confirm the medical device 20 is in use with the number of verification processes that indicate the medical device 20 is not in use, as shown at block 708. The main processing device 48 of the fluid management system 10 may then determine if a majority of the verification processes confirm the medical device 20 is in use, as shown at block 710. If the majority of the verification processes confirm the medical device 20 is in use, the fluid management system 10 determines the pressure data from the medical device 20 can be used to control the fluid flow from the fluid management system 10, as shown at block 712. If the majority of the verification processes do not or fails to confirm the medical device 20 is in use, the fluid management system 10 determines the pressure data from the medical device 20 cannot or should not be used to control the fluid flow from the fluid management system 10, as shown at block 714. In some cases, all of the verification processes may confirm the medical device 20 is in use while in other cases, all of the verification processes may be in agreement that the medical device is not in use 20.

Alternatively, or additionally to determining if a majority of the verification processes confirm or do not confirm the medical device 20 is in user, when at least one verification process returns a result that is different from the one or more additional verification processes, the main processing device 48 of the fluid management system 10 may be configured to apply a weighted average to the results. For example, if a verification process is deemed to be more accurate than other verification processes, the more accurate verification process may be weighted more heavily during the comparison step (block 708) than the other processes. Other techniques for comparing and analyzing the results from the verification processes may be used as desired.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A fluid management and medical device system comprising:
   a fluid management system comprising:
      a pump configured to pump fluid from a fluid supply source through the fluid management system at a fluid flow rate; and
      a processing device including a user interface, the processing device configured to control the pump to maintain a target fluid flow rate based on a set of system operating parameters;
   a medical device comprising:
      an elongate shaft in fluid communication with the pump of the fluid management system;
      a pressure sensor disposed at a distal end of the elongate shaft;
      a handle coupled to a proximal end of the elongate shaft; and
   wherein the processing device of the fluid management system is configured to adjust the fluid flow rate based on data received from the pressure sensor of the medical device;
   wherein the processing device of the fluid management system is configured to verify the medical device is in a patient's body and connected to the fluid management system prior to adjusting the fluid flow rate based on the data received from the pressure sensor of the medical device; and
   wherein the processing device is configured to perform the medical device verification each time the fluid management system attempts to use pressure data from the medical device to control fluid flow from the fluid management system.

2. The fluid management and medical device system of claim 1, wherein the processing device of the fluid management system is configured to compare a pulsatile pressure generated at the pump with the data received from the pressure sensor of the medical device; and
   wherein the pulsatile pressure generated at the pump and the data received from the pressure sensor of the medical device are each filtered, normalized, and converted to a frequency domain.

3. The fluid management and medical device system of claim 2, wherein when a dominant tone extracted from the frequency domain of the pulsatile pressure generated at the pump matches a dominant tone extracted from the frequency domain of the data received from the pressure sensor, the processing device of the fluid management system determines the medical device is in use within the patient's body.

4. The fluid management and medical device system of claim 1, further comprising a temperature sensor disposed at the distal end of the elongate shaft of the medical device; and
   wherein when a temperature measured at the temperature sensor is greater than a threshold temperature above room temperature, the processing device of the fluid management system determines the medical device is in use within the patient's body.

5. The fluid management and medical device system of claim 1, further comprising a stress sensor disposed at the distal end of the elongate shaft of the medical device; and
   wherein when a stress measured with the stress sensor is above a predetermined threshold, the processing device of the fluid management system determines the medical device is in use within the patient's body.

6. The fluid management and medical device system of claim 1, wherein the medical device further comprises a workstation in electronic communication with the pressure sensor and the processing device of the fluid management system, the workstation including at least a display and a processor.

7. The fluid management and medical device system of claim 1, further comprising:
   a position marker at the distal end of the elongate shaft of the medical device, the position marker configured for use in sensing in a magnetic field of a mapping and navigation system; and
   wherein a position of the position marker is determined relative to the patient.

8. The fluid management and medical device system of claim 7, wherein when the position of the position marker is within the patient's body, the processing device of the fluid management system determines the medical device is in use within the patient's body.

9. The fluid management and medical device system of claim 1, wherein the processing device of the fluid management system is configured to compare a pulsatile pressure generated within the patient's body with the data received from the pressure sensor of the medical device, and when a characteristic extracted from the data received from the pressure sensor of the medical device matches a characteristic extracted from the pulsatile pressure, the processing device of the fluid management system determines the medical device is in use within the patient's body.

10. The fluid management and medical device system of claim 1, wherein the processing device of the fluid management system is configured to compare an atmospheric pressure with the data received from the pressure sensor of the medical device while the pump is active, and when the data received from the pressure sensor of the medical device is greater than the atmospheric pressure, the processing device of the fluid management system determines the medical device is in use within the patient's body.

11. A fluid management and medical device system comprising:
- a fluid management system comprising:
  - a pump configured to pump fluid from a fluid supply source through the fluid management system at a fluid flow rate; and
  - a processing device including a user interface, the processing device configured to control the pump to maintain a target fluid flow rate based on a set of system operating parameters;
- a medical device comprising:
  - an elongate shaft in fluid communication with the pump of the fluid management system;
  - a pressure sensor disposed at a distal end of the elongate shaft;
  - a handle coupled to a proximal end of the elongate shaft; and
- wherein the processing device of the fluid management system is configured to adjust the fluid flow rate based on data received from the pressure sensor of the medical device;
- wherein the processing device of the fluid management system is configured to verify the medical device is in a patient's body and connected to the fluid management system using at least a first verification process and a second verification process prior to adjusting the fluid flow rate based on the data received from the pressure sensor of the medical device; and
- wherein the first verification process comprises:
  - comparing an atmospheric pressure with the data received from the pressure sensor of the medical device while the pump is active, and when the data received from the pressure sensor of the medical device is greater than the atmospheric pressure, the processing device of the fluid management system determines the medical device is in use within the patient's body.

12. The fluid management and medical device system of claim 11, wherein the processing device is further configured to use a third verification process prior to adjusting the fluid flow rate based on the data received from the pressure sensor of the medical device.

13. The fluid management and medical device system of claim 12, wherein each of the first verification process, the second verification process, and the third verification process are different.

14. The fluid management and medical device system of claim 12, wherein if a majority of the first verification process, the second verification process, and the third verification process indicate the medical device is in the patient's body, the processing device of the fluid management system determines the medical device is in use within the patient's body.

15. The fluid management and medical device system of claim 12, wherein the processing device of the fluid management system is configured to use a weighted average of a result from each of the first verification process, the second verification process, and the third verification process to determine if the medical device is in use within the patient's body.

16. A fluid management and medical device system comprising:
- a fluid management system comprising:
  - a pump configured to pump fluid from a fluid supply source through the fluid management system at a fluid flow rate; and
  - a processing device including a user interface, the processing device configured to control the pump to maintain a target fluid flow rate based on a set of system operating parameters;
- a medical device comprising:
  - an elongate shaft in fluid communication with the pump of the fluid management system;
  - a pressure sensor disposed at a distal end of the elongate shaft;
  - a handle coupled to a proximal end of the elongate shaft; and
- wherein the processing device of the fluid management system is configured to adjust the fluid flow rate based on data received from the pressure sensor of the medical device; and
- wherein the processing device of the fluid management system is configured to verify the medical device is in use within a patient's body based on one or more of pressure data, temperature measurement, stress measurement and position measurement obtained at the distal end of the elongate shaft of the medical device, prior to adjusting the fluid flow rate based on the data received from the pressure sensor of the medical device.

17. The fluid management and medical device system of claim 16, wherein the processing device of the fluid management system is configured to compare a pulsatile pressure generated at the pump with the data received from the pressure sensor of the medical device; and
- wherein the pulsatile pressure generated at the pump and the data received from the pressure sensor of the medical device are each filtered, normalized, and converted to a frequency domain.

18. The fluid management and medical device system of claim 16, further comprising a temperature sensor disposed at the distal end of the elongate shaft of the medical device; and
- wherein when a temperature measured at the temperature sensor is greater than a threshold temperature above room temperature, the processing device of the fluid management system determines the medical device is in use within the patient's body.

* * * * *